(12) United States Patent
Bailey

(10) Patent No.: US 9,085,582 B2
(45) Date of Patent: Jul. 21, 2015

(54) BENZOTRIAZOLODIAZEPINE COMPOUNDS INHIBITORS OF BROMODOMAINS

(75) Inventor: James Matthew Bailey, Stevenage (GB)

(73) Assignee: GlaxoSmithKline LLC, Wilmington, DE (US)

( * ) Notice: Subject to any disclaimer, the term of this patent is extended or adjusted under 35 U.S.C. 154(b) by 73 days.

(21) Appl. No.: 13/702,177

(22) PCT Filed: Jun. 20, 2011

(86) PCT No.: PCT/EP2011/060179
§ 371 (c)(1),
(2), (4) Date: Dec. 5, 2012

(87) PCT Pub. No.: WO2011/161031
PCT Pub. Date: Dec. 29, 2011

(65) Prior Publication Data
US 2013/0079335 A1  Mar. 28, 2013

(30) Foreign Application Priority Data

Jun. 22, 2010 (GB) .................................. 1010514.6
Apr. 21, 2011 (GB) .................................. 1106801.2

(51) Int. Cl.
*A61K 31/5517* (2006.01)
*C07D 487/04* (2006.01)
*A61K 45/06* (2006.01)

(52) U.S. Cl.
CPC .......... *C07D 487/04* (2013.01); *A61K 31/5517* (2013.01); *A61K 45/06* (2013.01)

(58) Field of Classification Search
CPC .......................... A61K 31/5517; C07D 487/04
USPC .......................................... 514/220; 540/566
See application file for complete search history.

(56) References Cited

U.S. PATENT DOCUMENTS

| 5,116,971 A | 5/1992 | Harreus et al. |
| 8,697,725 B2 | 4/2014 | Demont et al. |
| 2005/0222034 A1 | 10/2005 | Hsu |

FOREIGN PATENT DOCUMENTS

| CA | 2710740 A1 | 7/2009 |
| EP | 0638560 | 2/1995 |
| EP | 0792880 | 9/1997 |
| EP | 0934940 | 8/1999 |
| EP | 0989131 | 3/2000 |
| EP | 1887008 | 2/2008 |
| EP | 2239264 | 10/2010 |
| JP | 6128257 | 5/1994 |
| JP | 2008156311 | 7/2008 |
| WO | WO 95/14694 | 6/1995 |
| WO | WO 97/47622 | 12/1997 |
| WO | WO 2006/032470 | 3/2006 |
| WO | WO 2009/084693 | 7/2009 |

OTHER PUBLICATIONS

Database WPI Week 200137 Thomson Scientific, London, GB; AN 2001-355895 XP002615613 and WO 01/38377 A1 (Bioroad Gene Dev Ltd Shanghai) May 31, 2001 abstract.
Database WPI Week 200167. Thomson Scientific, London, GB; AN 2001-597108XP002615614 and WO 01/72812 A1 (Bode Gene Dev Co Ltd, Shanghai) Oct. 4, 2001 abstract.
Huang, Bo, et al; Brd4 Coactivates Transcriptional Activation of NF-kappa B via Specific Binding to Acetylated RelA; Molecular and Cellular Biology; Mar. 2009; vol. 29, No. 5; 1375-1387.
Wang, F., et al.; Brd2 disruption in mice causes severe obesity without Type 2 diabetes; Biochemical Journal; Nov. 2, 2009; vol. 425, No. Part 1; 71-83 + Suppl p. 81 para 1.
Bock M.G, et al; Cholecystokinin Antagonists. Synthesis and Biological Evaluation of 4-substituted 4H-U1,2,4 3/4 Triazolou4, 3-A 3/4 U1,4 3/4 Benzodiazepines; Journal of Medicinal Chemistry, American Chemical Society; vol. 31, No. 1; 176-180, 1988.
CAPLUS printout of JP 06128257, 1994.

*Primary Examiner* — Brenda Coleman
(74) *Attorney, Agent, or Firm* — Robert H. Brink

(57) ABSTRACT

Benzodiazepine compounds, pharmaceutical compositions containing such compounds and to their use in therapy.

29 Claims, No Drawings

BENZOTRIAZOLODIAZEPINE COMPOUNDS INHIBITORS OF BROMODOMAINS

CROSS-REFERENCE TO RELATED APPLICATIONS

This application is filed pursuant to 35 USC 371 as a United States National Phase Application of International Patent Application Serial No. PCT/EP2011/060179 filed on Jun. 20, 2011, which claims priority from 101514.6 filed on Jun. 22, 2010 and 1106801.2 filed on Apr. 21, 2011 in the United Kingdom.

FIELD OF THE INVENTION

The present invention relates to benzodiazepine compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nuclesome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine resides in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogensesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693A1 discloses a series of thienotriazolodiazepiene derivatives that are said to inhibit the binding between an acetylated histone and a bromodomain containing protein which are said to be useful as anti-cancer agents.

PCT patent application PCT/EP2010/066699 discloses a series of benzodiazapine derivatives that inhibit the binding of BET family bromodomains with acetylated lysine residues.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof.

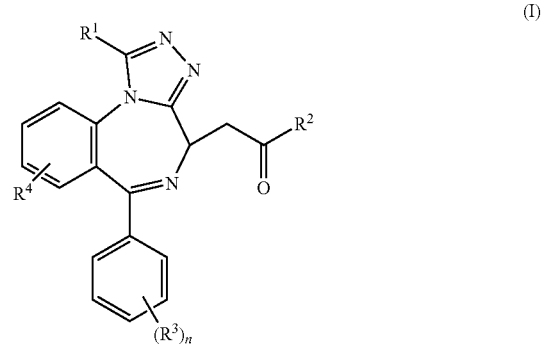

(I)

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof.

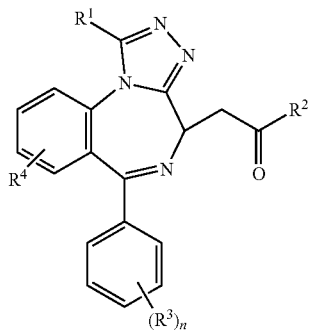

(I)

where
$R^1$ is $C_{1-3}$alkyl;
$R^2$ is —$NR^{2a}R^{2a'}$ or —$OR^{2b}$;
wherein one of $R^{2a}$ or $R^{2'a}$ is hydrogen, and $R^{2b}$ or the other of $R^{2a}$ or $R^{2'a}$ are selected from $C_{1-6}$alkyl, halo$C_{1-6}$alkyl, $R^{2c}R^{2'c}N$—$C_{1-6}$alkyl, carbocyclyl, carbocyclyl$C_{1-4}$alkyl, heterocyclyl and heterocyclyl$C_{1-4}$alkyl,
wherein any of the carbocyclyl or heterocyclyl groups are optionally substituted by one or more groups selected from halogen, $C_{1-6}$alkyl, halo$C_{1-6}$alkyl, $C_{1-6}$alkoxy, halo$C_{1-6}$alkoxy, carbonyl, —CO-carbocyclyl, azido, amino, hydroxyl, nitro and cyano,
wherein the —CO-carbocyclyl group may be further optionally substituted by one or more groups selected from halogen, $C_{1-6}$alkyl, halo$C_{1-6}$alkyl, $C_{1-6}$alkoxy, halo$C_{1-6}$alkoxy, azido, nitro and cyano;
or two adjacent groups on any of the carbocyclyl or heterocyclyl groups together with the interconnecting atoms form a 5- or 6-membered ring which ring may contain 1 or 2 heteroatoms independently selected from O, S and N;
or $R^{2a}$ and $R^{2'a}$ together with the N-atom to which they are attached form a 5-, 6- or 7-membered ring which may optionally contain 1 or 2 heteroatoms independently selected from O, S and N; wherein the 5-, 6- or 7-membered ring may be further optionally substituted by $C_{1-6}$alkyl;
$R^{2c}$ and $R^{2'c}$ are independently hydrogen or $C_{1-6}$alkyl;
each $R^3$ is independently selected from hydrogen, hydroxy, halo, $C_{1-6}$alkyl, halo $C_{1-6}$alkyl, $C_{1-6}$alkoxy, halo $C_{1-6}$alkoxy, nitro, cyano, $CF_3$, —$OCF_3$, —$COOR^5$, —$C_{1-4}$alkyl$NR^6R^7$ and —$C_{1-4}$alkylOH;

$R^4$ is an aromatic carbocyclic or aromatic heterocyclyl group; wherein the aromatic carbocyclyl or heterocyclyl group is optionally substituted by one or more groups selected from halo, $C_{1-6}$alkyl, $C_{1-6}$alkoxy and a group $C_{1-4}$alkyl$NR^6R^7$;
$R^5$ is $C_{1-3}$alkyl;
at each occurrence $R^6$ and $R^7$ are independently hydrogen, $C_{1-6}$alkyl or $C(O)C_{1-6}$alkyl, or
$R^6$ and $R^7$ together with the N-atom to which they are attached form a 5-, 6- or 7-membered ring which optionally contains 1 or 2 further heteroatoms independently selected from O, S and N; wherein the 5-, 6- or 7-membered ring may be further optionally substituted by one or more $C_{1-6}$alkyl, —$C(O)C_{1-6}$alkyl, amino or hydroxyl groups; and
n is an integer 1 to 5.

In one embodiment there is provided a compound of formula (I)
where
$R^1$ is $C_{1-3}$alkyl;
$R^2$ is —$NR^{2a}R^{2a'}$ or —$OR^{2b}$;
wherein one of $R^{2a}$ or $R^{2'a}$ is hydrogen, and $R^{2b}$ or the other of $R^{2a}$ or $R^{2'a}$ are selected from $C_{1-6}$alkyl, halo$C_{1-6}$alkyl, $R^{2c}R^{2'c}N$—$C_{2-6}$alkyl $R^{2c}O$—$C_{2-6}$alkyl, carbocyclyl, carbocyclyl$C_{1-4}$alkyl, heterocyclyl and heterocyclyl$C_{1-4}$alkyl,
wherein any of the carbocyclyl or heterocyclyl groups are optionally substituted by one or more groups selected from halogen, $C_{1-6}$alkyl, halo$C_{1-6}$alkyl, $C_{1-6}$alkoxy, halo$C_{1-6}$alkoxy, carbonyl, —CO-carbocyclyl, amino, hydroxyl and cyano,
or two adjacent groups on any of the carbocyclyl or heterocyclyl groups together with the interconnecting atoms form a 5- or 6-membered ring which ring may contain 1 or 2 heteroatoms independently selected from O, S and N;
or $R^{2a}$ and $R^{2'a}$ together with the N-atom to which they are attached form a 5-, 6- or 7-membered ring which may optionally contain 1 or 2 heteroatoms independently selected from O, S and N; wherein the 5-, 6- or 7-membered ring may be further optionally substituted by $C_{1-6}$alkyl;
$R^{2c}$ and $R^{2'c}$ are independently hydrogen or $C_{1-6}$alkyl;
each $R^3$ is independently selected from hydrogen, hydroxy, halo, $C_{1-6}$alkyl, halo $C_{1-6}$alkyl, $C_{1-6}$alkoxy, halo $C_{1-6}$alkoxy, cyano, $CF_3$, —$OCF_3$, —$COOR^5$, —$C_{1-4}$alkyl$NR^6R^7$ and —$C_{1-4}$alkylOH;
$R^4$ is an aromatic carbocyclic or aromatic heterocyclyl group; wherein the aromatic carbocyclyl or heterocyclyl group is optionally substituted by one or more groups selected from halo, $C_{1-6}$alkyl, $C_{1-6}$alkoxy and a group $C_{1-4}$alkyl$NR^6R^7$
$R^5$ is $C_{1-3}$alkyl;
at each occurrence $R^6$ and $R^7$ are independently hydrogen, $C_{1-6}$alkyl or $C(O)C_{1-6}$alkyl, or
$R^6$ and $R^7$ together with the N-atom to which they are attached form a 5-, 6- or 7-membered ring which optionally contains 1 or 2 further heteroatoms independently selected from O, S and N; wherein the 5-, 6- or 7-membered ring may be further optionally substituted by one or more $C_{1-6}$alkyl, —$C(O)C_{1-6}$alkyl, amino or hydroxyl groups; and
n is an integer 1 to 5.

In one embodiment of the invention the S-enantiomers are preferred.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, n-hexyl, isobutyl, isopropyl, t-butyl and 1,1-dimethylpropyl.

As used herein, the term "alkoxy" refers to a straight or branched alkoxy group containing the specified number of carbon atoms. For example, $C_{1-6}$alkoxy means a straight or branched alkoxy group containing at least 1, and at most 6, carbon atoms. Examples of "alkoxy" as used herein include, but are not limited to, methoxy, ethoxy, propoxy, prop-2-oxy, butoxy, but-2-oxy, 2-methylprop-1-oxy, 2-methylprop-2-oxy, pentoxy or hexyloxy.

As used herein, the term "halogen" or "halo" refers to the elements fluorine, chlorine, bromine and iodine. Examples of suitable halogens are fluorine, chlorine and bromine.

Unless otherwise indicated, any carbocyclyl group contains 3 to 8 ring-atoms, and may be saturated, unsaturated or aromatic. Examples of saturated carbocyclyl groups include cyclopropyl, cyclopentyl or cyclohexyl. Examples of unsaturated carbocyclyl groups include those which contain up to 3 double bonds. An example of a suitable aromatic carbocyclyl group is phenyl. The term carbocylic should be similarly construed. In addition, the term carbocyclyl includes any fused combination of carbocyclyl groups, for example naphthyl, anthryl, phenanthryl, indanyl, indenyl, azulenyl, azulanyl, and fluorenyl.

Unless otherwise indicated, any heterocyclyl group contains 5 to 7 ring-atoms up to 4 of which may be hetero-atoms such as nitrogen, oxygen and sulfur, and may be saturated, unsaturated or aromatic. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl, piperidinyl, homopiperazinyl, dioxanyl, morpholino, dithianyl, thiomorpholino, thiomorpholino-1,1-dioxide, pyridazinyl, pyrimidinyl, pyrazinyl, piperazinyl, sulfolanyl, tetrazolyl, triazinyl, azepinyl, oxazepinyl, thiazepinyl, diazepinyl and thiazolinyl. In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

As used herein, the term "substituted" refers to substitution with the named substituent or substituents. With multiple degrees of substitution (e.g. 1 or 2) the groups can be the same or different.

In one embodiment, $R^1$ is methyl.

In one embodiment $R^2$ is $-OR^{2b}$. In a further embodiment $R^2$ is $-OR^{2b}$ in which $R^{2b}$ is $C_{1-6}$alkyl. In a yet further embodiment $R^{2b}$ is selected from methyl, ethyl, isopropyl and butyl.

In one embodiment $R^2$ is $-NR^{2a}R^{2a'}$.

In another embodiment $R^2$ is $-NR^{2a}R^{2a'}$ in which $R^{2a}$ is hydrogen and $R^{2'a}$ is $C_{1-6}$alkyl. In a further embodiment $R^{2'a}$ is ethyl.

In another embodiment $R^2$ is $-NR^{2a}R^{2a'}$ in which $R^{2a}$ is hydrogen and $R^{2'a}$ is $R^{2c}R^{2'c}N-C_{1-6}$alkyl. In another embodiment $R^{2'a}$ is selected from $R^{2c}R^{2'c}N-CH_2CH_2-$, $R^{2c}R^{2'c}N-CH_2CH_2CH_2-$ and $R^{2c}R^{2'c}N-CH_2CH_2CH_2CH_2-$. In a further embodiment $R^{2c}$ and $R^{2'c}$ are selected from hydrogen and methyl.

In another embodiment $R^2$ is $-NR^{2a}R^{2a'}$ in which $R^{2a}$ is hydrogen and $R^{2'a}$ is carbocyclyl. In a further embodiment $R^{2'a}$ is cyclopentyl or cyclohexyl, wherein each group is optionally substituted once by amino or hydroxyl.

In another embodiment $R^2$ is $-NR^{2a}R^{2a'}$ in which $R^{2a}$ is hydrogen and $R^{2'a}$ is heterocyclyl. In another embodiment $R^{2'a}$ is selected from pyrrolidinyl, piperidinyl, tetrahydrofuranyl and tetrahydropyran, wherein each group is optionally substituted by $C_{1-6}$alkyl. In a further embodiment $R^{2'a}$ is selected from:

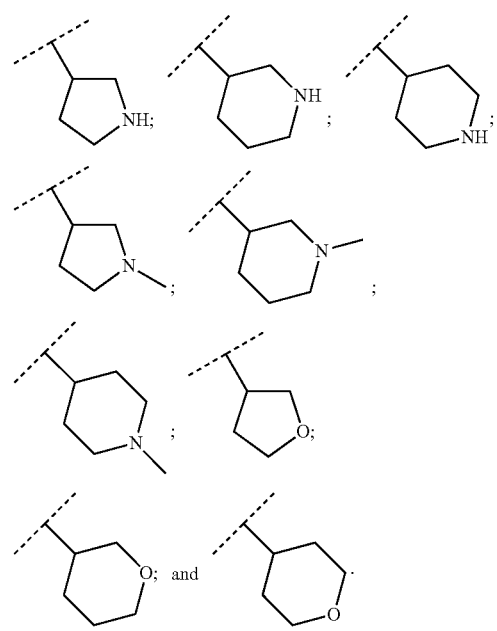

In another embodiment $R^2$ is $-NR^{2a}R^{2a'}$ in which $R^{2a}$ is hydrogen and $R^{2'a}$ is heterocyclyl$C_{1-4}$alkyl, wherein the heterocyclyl is optionally substituted once by amino, hydroxyl or methyl. In another embodiment $R^{2'a}$ is selected from heterocyclyl-$CH_2-$, heterocyclyl-$CH_2CH_2-$, heterocyclyl-$CH_2CH_2CH_2-$ and heterocyclyl-$CH_2CH_2CH_2CH_2-$, wherein the heterocyclyl is optionally substituted once by amino, hydroxyl or methyl. In another embodiment heterocyclyl is selected from pyrrolidinyl, piperidinyl, tetrahydropyranyl, piperazinyl, morpholino and thiomorpholinodioxide, wherein each group is optionally substituted once by amino, hydroxyl or methyl. In a further embodiment heterocyclyl is selected from:

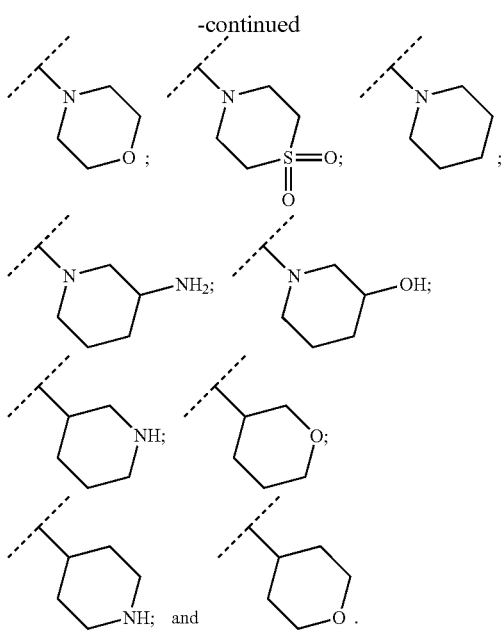

n may for example represent an integer in the range 1 to 3 such as 1.

In one embodiment, $R^3$ is halo, $C_{1-6}$alkyl, $C_{1-6}$alkoxy or $CF_3$. In another embodiment, $R^3$ is chloro, fluoro, methoxy or $CF_3$. In a further embodiment, $R^3$ is 3-fluoro, 4-chloro, 4-fluoro, 4-methoxy, or 4-$CF_3$. In a further embodiment $R^3$ is 4-chloro.

In one embodiment $R^4$ is phenyl, pyridyl, imadolzolyl or pyrazolyl, such groups being optionally substituted by one or more groups selected from halo, $C_{1-6}$alkyl, $C_{1-6}$alkoxy or a group $C_{1-4}$alkyl$NR^6R^7$ in which $R^6$ is hydrogen and $R^7$ is hydrogen, $C_{1-6}$alkyl or $C(O)C_{1-6}$alkyl. In a further embodiment $R^4$ is selected from

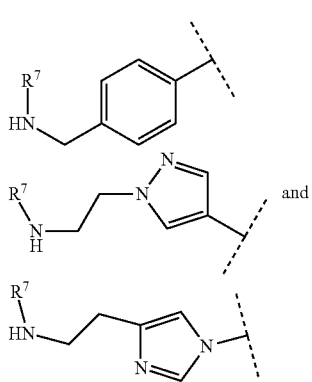

in which $R^7$ is hydrogen, methyl or C(O)Me.

In one embodiment $R^4$ is phenyl substituted by a group $C_{1-4}$alkyl$NR^6R^7$ in which $R^6$ and $R^7$ together with the N-atom to which they are attached form a pyrrolidinyl, piperazinyl, piperidinyl or morpholinyl ring said rings being optionally substituted by one or more (e.g 2) $C_{1-6}$alkyl (such as methyl), —C(O)$C_{1-6}$alkyl (such as COMe), amino or hydroxyl groups. In a further embodiment $R^4$ is phenyl substituted by a group $CH_2NR^6R^7$ in which $R^6$ and $R^7$ together with the N-atom to which they are attached form a pyrrolidinyl ring or a piperazinyl ring substituted by a methyl group.

In one embodiment the $R^4$ group is at the 8 position of the benzodiazepine ring.

While the embodiments for each variable have generally been listed above separately for each variable this invention includes those compounds in which several or each embodiment in formula (I) is selected from each of the embodiments listed above. Therefore, this invention is intended to include all combinations of embodiments for each variable described hereinabove including salts thereof.

In one embodiment, there is a compound which is selected from

2-[(4S)-6-(4-Chlorophenyl)-1-methyl-8-phenyl-4H-[1,2,4]triazolo[4,3-a][1,4]benzodiazepin-4-yl]-N-ethylacetamide;

Ethyl [(4S)-6-(4-Chlorophenyl)-1-methyl-8-(4-pyridinyl)-4H-[1,2,4]triazolo[4,3-a][1,4]benzodiazepin-4-yl]acetate;

2-{(4S)-6-(4-Chlorophenyl)-1-methyl-8-[4-(methyloxy)phenyl]-4H-[1,2,4]triazolo[4,3-a][1,4]benzodiazepin-4-yl}-N-ethylacetamide;

2-[(4S)-6-(4-Chlorophenyl)-1-methyl-8-(1H-pyrazol-5-yl)-4H-[1,2,4]triazolo[4,3-a][1,4]benzodiazepin-4-yl]-N-ethylacetamide;

2-[(4S)-6-(4-Chlorophenyl)-1-methyl-8-(1H-pyrazol-4-yl)-4H-[1,2,4]triazolo[4,3-a][1,4]benzodiazepin-4-yl]-N-ethylacetamide;

2-[(4S)-6-(4-Chlorophenyl)-1-methyl-8-(2-methylphenyl)-4H-[1,2,4]triazolo[4,3-a][1,4]benzodiazepin-4-yl]-N-ethylacetamide;

2-[(4S)-6-(4-Chlorophenyl)-1-methyl-8-(3-pyridinyl)-4H-[1,2,4]triazolo[4,3-a][1,4]benzodiazepin-4-yl]-N-ethylacetamide;

(S)-2-(6-(4-Chlorophenyl)-8-(3-methoxyphenyl)-1-methyl-4H-benzo[f][1,2,4]triazolo[4,3-a][1,4]diazepin-4-yl)-N-ethylacetamide;

(S)-2-(6-(4-Chlorophenyl)-1-methyl-8-(pyridin-4-yl)-4H-benzo[f][1,2,4]triazolo[4,3-a][1,4]diazepin-4-yl)-N-ethylacetamide;

(S)-2-(6-(4-Chlorophenyl)-1-methyl-8-(3-((4-methylpiperazin-1-yl)methyl)phenyl)-4H-benzo[f][1,2,4]triazolo[4,3-a][1,4]diazepin-4-yl)-N-ethylacetamide;

(S)-2-(6-(4-Chlorophenyl)-8-(3-((ethylamino)methyl)phenyl)-1-methyl-4H-benzo[f][1,2,4]triazolo[4,3-a][1,4]diazepin-4-yl)-N-ethylacetamide;

(S)-2-(6-(4-Chlorophenyl)-1-methyl-8-(3-(pyrrolidin-1-ylmethyl)phenyl)-4H-benzo[f][1,2,4]triazolo[4,3-a][1,4]diazepin-4-yl)-N-ethylacetamide;

(S)-2-(6-(4-Chlorophenyl)-1-methyl-8-(4-(pyrrolidin-1-ylmethyl)phenyl)-4H-benzo[f][1,2,4]triazolo[4,3-a][1,4]diazepin-4-yl)-N-ethylacetamide;

(S)-2-(6-(4-Chlorophenyl)-1-methyl-8-(4-((4-methylpiperazin-1-yl)methyl)phenyl)-4H-benzo[f][1,2,4]triazolo[4,3-a][1,4]diazepin-4-yl)-N-ethylacetamide;

(S)-2-(6-(4-Chlorophenyl)-8-(4-((ethylamino)methyl)phenyl)-1-methyl-4H-benzo[f][1,2,4]triazolo[4,3-a][1,4]diazepin-4-yl)-N-ethylacetamide;

(S)-2-(6-(4-Chlorophenyl)-8-(4-((dimethylamino)methyl)phenyl)-1-methyl-4H-benzo[f][1,2,4]triazolo[4,3-a][1,4]diazepin-4-yl)-N-ethylacetamide; and (S)-2-(6-(4-Chlorophenyl)-1-methyl-8-(2H-tetrazol-5-yl)-4H-benzo[f][1,2,4]triazolo[4,3-a][1,4]diazepin-4-yl)-N-ethylacetamide or a salt thereof.

In a particular embodiment there is provided (S)-2-(6-(4-chlorophenyl)-1-methyl-8-(4-(pyrrolidin-1-ylmethyl)phenyl)-4H-benzo[f][1,2,4]triazolo[4,3-a][1,4]diazepin-4-yl)-N-ethylacetamide or a salt thereof.

It will be appreciated that the present invention covers compounds of formula (I) as the free base and as salts thereof, for example as a pharmaceutically acceptable salt thereof. In one embodiment the invention relates to compounds of formula (I) as the free base. In another embodiment the invention to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated, for example, by crystallisation and filtration. A pharmaceutically acceptable acid addition salt of a compound of formula (I) can comprise or be, for example, a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example, in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) and pharmaceutically acceptable salts thereof, which upon administration to the recipient are capable of providing (directly or indirectly) a compound of formula (I) or a pharmaceutically acceptable salts thereof, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The compounds described herein contain one or more chiral atoms so that optical isomers, e.g.—enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures).

Similarly the invention also extends to conformational isomers of compounds of formula (I) and any geometric (cis and/or trans) isomers of said compounds.

An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compound of formula (I) and pharmaceutically acceptable salts thereof may be made by a variety of methods, including standard chemistry. Any previously defined variable will continue to have the previously defined meaning unless otherwise indicated. Illustrative general synthetic methods are set out below.

The compounds of formula (I) may be prepared by the methods described in Scheme 1.

Scheme 1
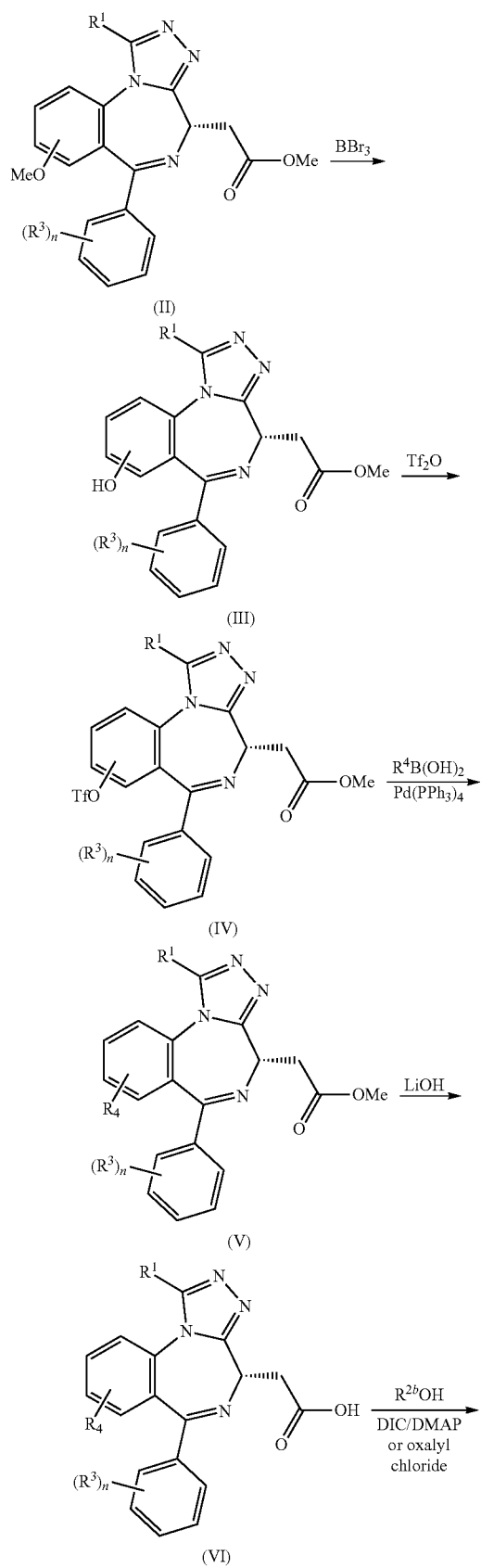
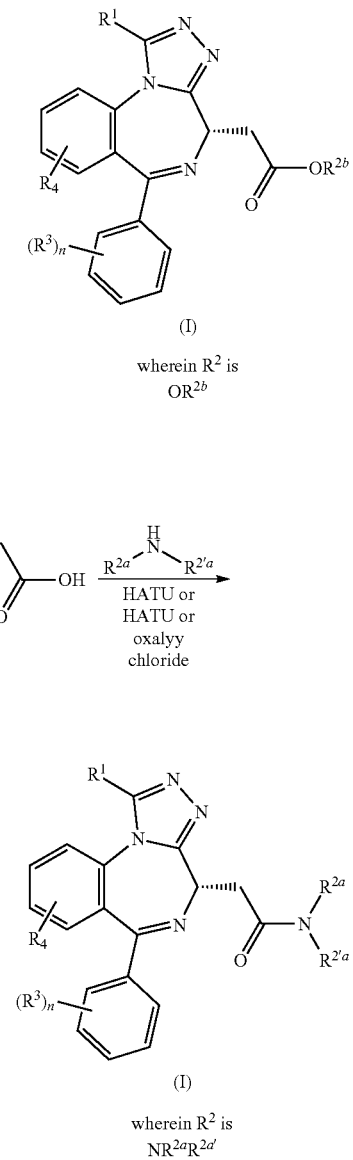
Compounds of formula (II) may be prepared in accordance with the methods described in Scheme 2.
Scheme 2
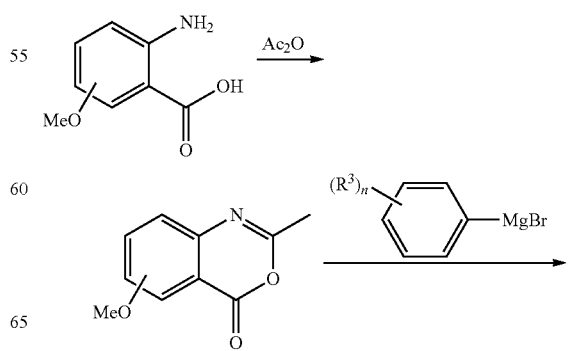

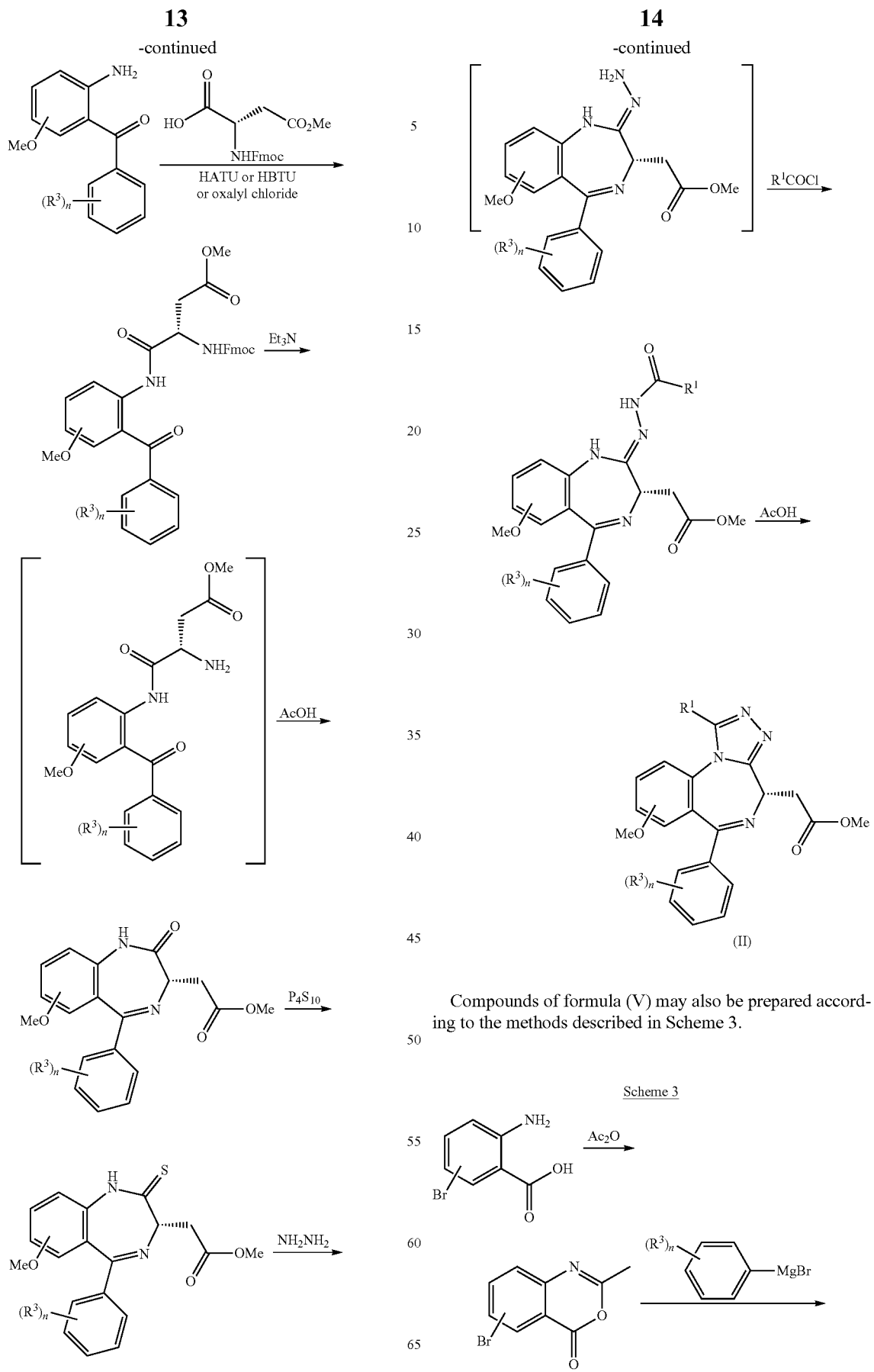
Compounds of formula (V) may also be prepared according to the methods described in Scheme 3.
Scheme 3

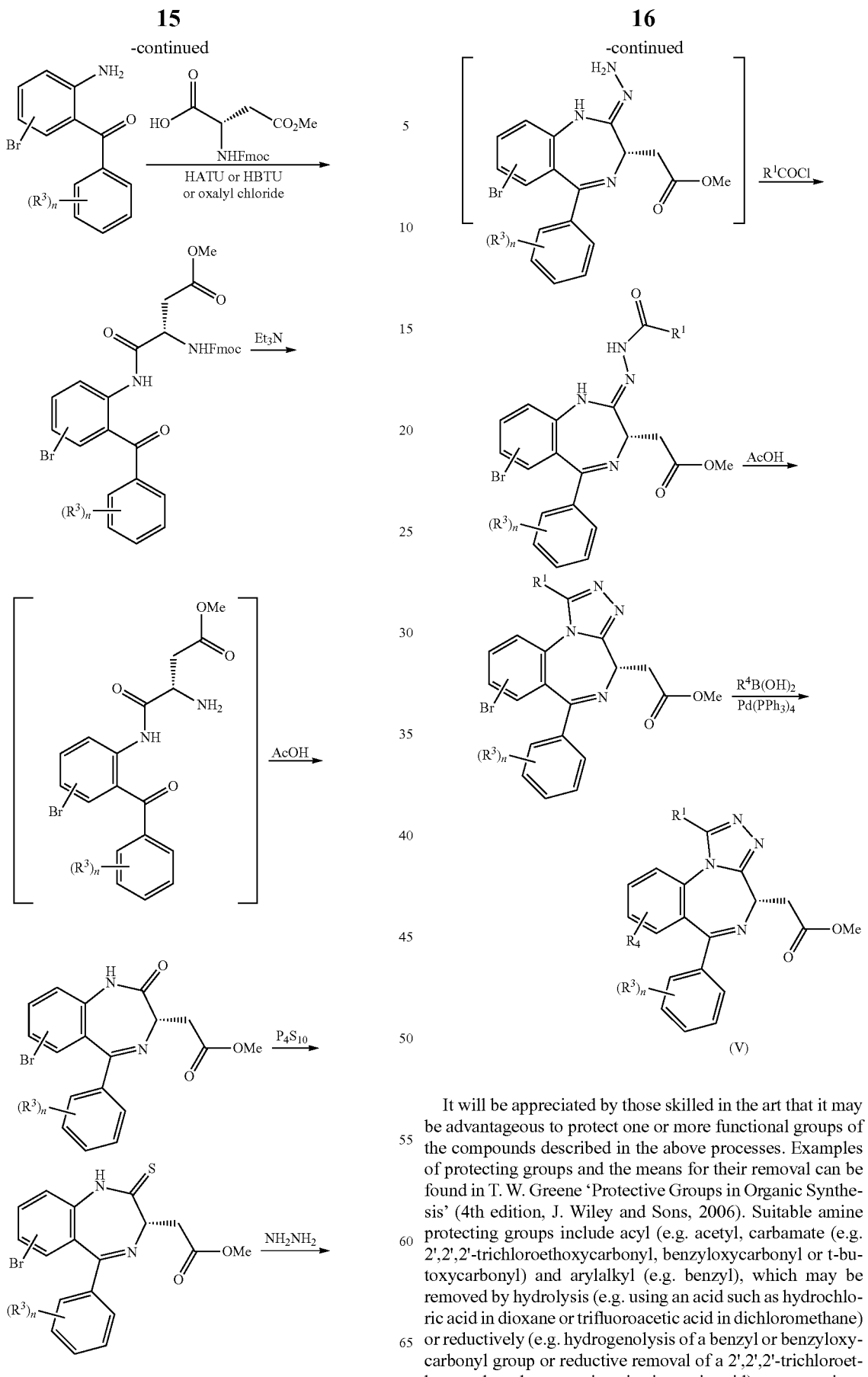

It will be appreciated by those skilled in the art that it may be advantageous to protect one or more functional groups of the compounds described in the above processes. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate.

Other suitable amine protecting groups include trifluoroacetyl (—COCF₃) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above are believed to be novel and therefore form a yet further aspect of the invention.

The compounds of formula (I) and salts thereof are bromodomain inhibitors, and thus to believed to have potential utility in the treatment of diseases or conditions for which a bromodomain is indicated.

The present invention thus provides a compound of formula (I) or a pharmaceutically acceptable salt thereof for use in therapy. The compound of formula (I) or pharmaceutically salt thereof can be for use in the treatment of diseases or conditions for which a bromodomain inhibitor indicated.

In one embodiment there is provided a compound of formula (I) or a pharmaceutically acceptable salt thereof for use in the treatment of diseases or conditions for which a bromodomain is indicated. In another embodiment, there is provided a compound or a pharmaceutically acceptable salt thereof for use in the treatment of a chronic autoimmune and/or inflammatory condition. In a further embodiment, there is provided a compound or a pharmaceutically acceptable salt thereof for use in the treatment of cancer, such as midline carcinoma.

In one embodiment there is provided the use of a compound of formula (I) or a pharmaceutically acceptable salt thereof in the manufacture of a medicament for the treatment of diseases or conditions for which a bromodomain inhibitor is indicated. In another embodiment, there is provided the use of a compound of formula (I) or a pharmaceutically acceptable salt thereof in the manufacture of a medicament for the treatment of a chronic autoimmune and/or inflammatory condition. In a further embodiment, there is provided the use of a compound of formula (I) or a pharmaceutically acceptable salt thereof in the manufacture of a medicament for the treatment of cancer, such as midline carcinoma.

In one embodiment there is provided a method for treatment of a disease or condition, for which a bromodomain inhibitor is indicated, in a subject in need thereof which comprises administering a therapeutically effective amount of compound of formula (I) or a pharmaceutically acceptable salt thereof. In another embodiment there is provided a method for treatment of a chronic autoimmune and/or inflammatory condition, in a subject in need thereof which comprises administering a therapeutically effective amount of compound of formula (I) or a pharmaceutically acceptable salt thereof. In a further embodiment there is provided a method for treatment of cancer, such as midline carcinoma, in a subject in need thereof which comprises administering a therapeutically effective amount of compound of formula (I) or a pharmaceutically acceptable salt thereof.

In one embodiment the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, dry eye, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritism, pyoderma gangrenosum and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, and pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma, and cardiac fibrosis.

Bromodomain inhibitors may be useful in the prevention and treatment of viral infections such as herpes virus, human papilloma virus, adenovirus, poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, hemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, hemorrhage, extensive tissue damage, SIRS or MODS. In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or acute on chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, human immunodeficiency virus (HIV), cervical neoplasia, adenovirus infections, including acute respiratory disease, and poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include all of the above disease states.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of the formula (I), or a pharmaceutically acceptable salt thereof, with one or more pharmaceutically acceptable carriers, diluents or excipients. The pharmaceutical composition can be for use in the treatment of any of the conditions described herein.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration (e.g. topical administration to the skin or the eye).

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, as, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds compound of formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel or spray foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Dosage forms for nasal or inhaled administration may conveniently be formulated as aerosols, solutions, suspensions, gels or dry powders.

For compositions suitable and/or adapted for inhaled administration, it is preferred that compounds of formula (I) or pharmaceutically acceptable salts thereof are in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compound of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or pharmaceutically acceptable salts thereof calculated as the free base. Each dosage unit for nasal or inhaled administration preferably contains from 0.001 to 50 mg, more preferably 0.01 to 5 mg, of a compound of formula (I) or a pharmaceutically acceptable salt thereof, calculated as the free base.

The pharmaceutically acceptable compound of formula (I) and pharmaceutically acceptable salts thereof can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compound of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound of formula (I) and pharmaceutically acceptable salts thereof and the other pharmaceutically active agent(s) may be administered together in a single pharmaceutical composition or separately and, when administered separately this may occur simultaneously or sequentially in any order. The amounts of the compound of formula (I) and pharmaceutically acceptable salts thereof and the other pharmaceutically active agent (s) and the relative timings of administration will be selected in order to achieve the desired combined therapeutic effect. Thus in a further aspect, there is provided a combination comprising a compound of formula (I) or pharmaceutically acceptable salts thereof and at least one other pharmaceutically active agent. In one embodiment there is provided a combination pharmaceutical product comprising a compound of formula (I) or a pharmaceutically acceptable salt thereof together with one or more other therapeutically active agents.

Thus in one aspect, the compound and pharmaceutical compositions according to the invention may be used in combination with or include one or more other therapeutic agents, for example selected from antibiotics, anti-virals, glucocorticosteroids, muscarinic antagonists, beta-2 agonists and Vitamin D3 analogues.

It will be appreciated that when the compound of the present invention is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

GENERAL EXPERIMENTAL DETAILS

All temperatures referred to are in ° C.

The names of the following compounds have been obtained using the compound naming programme "ACD Name Pro 6.02" or Chem Draw Ultra 12.0.

Abbreviations

AcOH refers to acetic acid
BINAP refers to 2,2'-bis(diphenylphosphino)-1,1'-binaphthyl
BOC refers to tert-butoxycarbonyl
CV refers to column volumes
DCM refers to dichloromethane
1,2-DCE refers to 1,2-dichloroethane
DIC refers to Diisoproylcarbodiimide
DIPEA refers to diisopropylethylamine
DMAP refers to 4-dimethylaminopyridine
DMSO refers to dimethylsulfoxide.
DME refers to 1,2-dimethoxyethanol
DMF refers to N,N-dimethylformamide
$Et_2O$ refers to diethyl ether
EtOAc refers to ethyl acetate
FMOC refers to 9-fluorenylmethoxycarbonyl
HATU refers to O-(7-azabenzotriazol-1-yl)-N,N,N',N'-tetramethyluronium hexafluorophosphate
HBTU refers to 0-(Benzotriazol-1-yl)-N,n,N',N' tetramethyluronium hexafluorophosphate
HPLC refers to high performance liquid chromatography
IPA refers to propan-2-ol
i-$Pr_2O$ refers to di-isopropyl ether
$LiAlH_4$ refers to lithium aluminium hydride LCMS=Liquid chromatography/mass spectrometry
MDAP=mass-directed autoprep/mass-directed HPLC
MeCN refers to acetonitrile
MeOH refers to methanol
$MgSO_4$ refers to magnesium sulfate
Mp refers to melting point
r.t. refers to room temperature
RT=retention time
$Na_2SO_4$ refers to sodium sulfate
TFA refers to trifluoroacetic acid
THF refers to tetrahydrofuran LCMS Methodology
Method Formate
LC Conditions The UPLC analysis was conducted on an Acquity UPLC BEH C18 column (50 mm×2.1 mm, i.d. 1.7 μm packing diameter) at 40° C.

The solvents employed were:
A=0.1% v/v solution of formic acid in water
B=0.1% v/v solution of formic acid in acetonitrile
The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions

| MS | Waters ZQ |
|---|---|
| Ionisation mode | Alternate-scan positive and negative electrospray |
| Scan range | 100 to 1000 AMU |
| Scan time | 0.27 sec |
| Inter scan delay | 0.10 sec |

MDAP Methodology
Method Formate Modifier
LC Conditions

The HPLC analysis was conducted on either a Sunfire C18 column (100 mm×19 mm, i.d 5 μm packing diameter) or a Sunfire C18 column (150 mm×30 mm, i.d. 5 μm packing diameter) at ambient temperature.

The solvents employed were:
A=0.1% v/v solution of formic acid in water
B=0.1% v/v solution of formic acid in acetonitrile Run as a gradient over either 15 or 25 min (extended run) with a flow rate of 20 ml/min (100 mm×19 mm, i.d 5 μm packing diameter) or 40 ml/min (150 mm×30 mm, i.d. 5 μm packing diameter).

The UV detection was a summed signal from wavelength of 210 nm to 350 nm.
MS Conditions

| MS | Waters ZQ |
|---|---|
| Ionisation mode | Alternate-scan positive and negative electrospray |
| Scan range | 100 to 1000 AMU |
| Scan time | 0.50 sec |
| Inter scan delay | 0.20 sec |

In the procedures that follow, after each starting material, reference to an Intermediate by number is typically provided. This is provided merely for assistance to the skilled chemist. The starting material may not necessarily have been prepared from the batch referred to.

Intermediate 1

[(4S)-6-(4-Chlorophenyl)-1-methyl-8-phenyl-4H-[1,2,4]triazolo[4,3-a][1,4]benzodiazepin-4-yl]acetic acid Sodium carbonate (35.8 mg), phenylboronic acid (22.5 mg) and bis(triphenylphosphine)palladium(II) chloride (10.8 mg) were added to a 2-5 ml microwave vial. A solution of ethyl ((4S)-6-(4-chlorophenyl)-1-methyl-8-{[(trifluoromethyl)sulfonyl]oxy}-4H-[1,2,4]triazolo[4,3-a][1,4]benzodiazepin-4-yl)acetate (for a preparation see Intermediate 2) (83.4 mg) in DME (3 ml) and water (1 ml) was added to the microwave vial. The reaction mixture was heated at 120° C. for 90 min (microwave). Ethyl acetate (2 ml) was added and the water layer was separated and acidified with glacial acetic acid. The water layer was extracted with ethyl acetate (3×5 ml) and the organic layer was dried and the solvent evaporated. The residue was chromatographed (0-10% methanol: DCM) to give [(4S)-6-(4-chlorophenyl)-1-methyl-8-phenyl-4H-[1,2,4]triazolo[4,3-a][1,4]benzodiazepin-4-yl]acetic acid as a white oil (30.1 mg), which was used without further purification in the subsequent reaction. LCMS (formate): $MH^+$ 443/445, RT 1.09 min Intermediate 2

Ethyl ((4S)-6-(4-chlorophenyl)-1-methyl-8-{[(trifluoromethyl)sulfonyl]oxy}-4H-[1,2,4]triazolo[4,3-a][1,4]benzodiazepin-4-yl)acetate Ethyl [(4S)-6-(4-chlorophenyl)-8-hydroxy-1-methyl-4H-[1,2,4]triazolo[4,3-a][1,4]benzodiazepin-4-yl]acetate (508 mg, for a preparation see intermediate 8) was dissolved in DCM (30 ml). Pyridine (500 µl) was added and the reaction mixture was stirred and cooled an ice bath. Triflic anhydride (251 µl) was added slowly. After addition the mixture was stirred in the ice bath for 2.5 h. The solvent was evaporated and the residue was chromatographed (0-5% methanol:DCM) to give ethyl ((4S)-6-(4-chlorophenyl)-1-methyl-8-{[(trifluoromethyl)sulfonyl]oxy}-4H-[1,2,4]triazolo[4,3-a][1,4]benzodiazepin-4-yl)acetate (295 mg) as an orange oil and further impure ethyl ((4S)-6-(4-chlorophenyl)-1-methyl-8-{[(trifluoromethyl)sulfonyl]oxy}-4H-[1,2,4]triazolo[4,3-a][1,4]benzodiazepin-4-yl)acetate. The impure material was chromatographed (0-5% methanol:DCM) to give the pure ethyl ((4S)-6-(4-chlorophenyl)-1-methyl-8-{[(trifluoromethyl)sulfonyl]oxy}-4H-[1,2,4]triazolo[4,3-a][1,4]benzodiazepin-4-yl)acetate (88 mg) as a white solid.

LCMS (formate): MH$^+$ 543/545, RT 1.22 min

Intermediate 3

(4S)-6-(4-Chlorophenyl)-4-[2-(ethylamino)-2-oxoethyl]-1-methyl-4H-[1,2,4]triazolo[4,3-a][1,4]benzodiazepin-8-yl trifluoromethanesulfonate

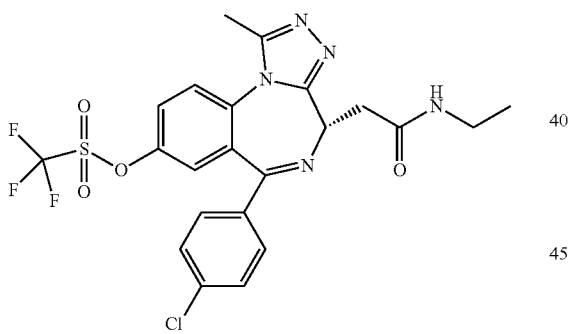

2-[(4S)-6-(4-Chlorophenyl)-8-hydroxy-1-methyl-4H-[1,2,4]triazolo[4,3-a][1,4]benzodiazepin-4-yl]-N-ethylacetamide (for a preparation see Intermediate 4) (104.2 mg) was dissolved in DCM (10 ml). DIPEA (53 µl) and N-phenyl-bis(trifluoromethanesulfonamide) (100 mg) were added and the reaction mixture was stirred at room temperature for 3.5 h. The solvent was evaporated and the residue was chromatographed (0-5% methanol:DCM) to give (4S)-6-(4-chlorophenyl)-4-[2-(ethylamino)-2-oxoethyl]-1-methyl-4H-[1,2,4]triazolo[4,3-a][1,4]benzodiazepin-8-yl trifluoromethanesulfonate as a white glassy solid (130 mg).

LCMS (formate): MH$^+$ 542/544, RT 1.10 min

Intermediate 4

2-[(4S)-6-(4-Chlorophenyl)-8-hydroxy-1-methyl-4H-[1,2,4]triazolo[4,3-a][1,4]benzodiazepin-4-yl]-N-ethylacetamide

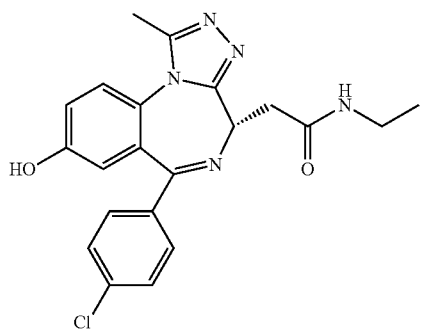

2-[(4S)-6-(4-Chlorophenyl)-1-methyl-8-(methyloxy)-4H-[1,2,4]triazolo[4,3-a][1,4]benzodiazepin-4-yl]-N-ethylacetamide (which may be prepared, for example, by reaction of Reference compound H with ethylamine) (0.424 g) was dissolved in DCM (8 ml) and cooled to −78° C. A solution of boron tribromide (0.945 ml) in DCM (2 ml) was added slowly to the reaction mixture. The reaction was stirred at −78° C. for 35 min under nitrogen and then at room temperature for 2.5 h. The reaction was quenched by adding a solution of ethanol (1 ml) in DCM (5 ml) dropwise. The solvent was evaporated and the residue was chromatographed (0-10% methanol:DCM) to give 2-[(4S)-6-(4-chlorophenyl)-8-hydroxy-1-methyl-4H-[1,2,4]triazolo[4,3-a][1,4]benzodiazepin-4-yl]-N-ethylacetamide as a yellow solid. The aqueous layer was passed through a pre equilibrated Biotage 103 column, the organic content was eluted with methanol and the methanolic solution was evaporated to give a further quantity of 2-[(4S)-6-(4-chlorophenyl)-8-hydroxy-1-methyl-4H-[1,2,4]triazolo[4,3-a][1,4]benzodiazepin-4-yl]-N-ethylacetamide as a yellow solid (total yield 271.3 mg).

LCMS (formate): MH$^+$ 410/412, RT 0.76 min

Intermediate 5

(S)-2-(6-(4-Chlorophenyl)-8-(3-formylphenyl)-1-methyl-4H-benzo[f][1,2,4]triazolo[4,3-a][1,4]diazepin-4-yl)-N-ethylacetamide

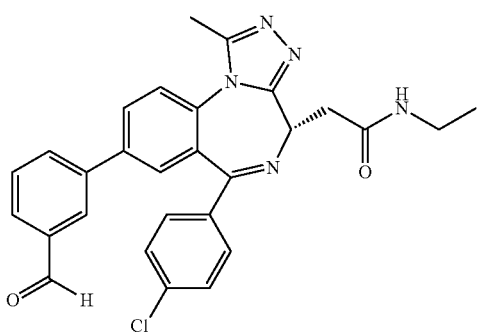 [SMILES: CCNC(=O)C[C@@H]1N=C(c2ccc(Cl)cc2)c2cc(-c3cccc(C=O)c3)ccc2-n2c(C)nnc21]

(S)-6-(4-Chlorophenyl)-4-(2-(ethylamino)-2-oxoethyl)-1-methyl-4H-benzo[f][1,2,4]triazolo[4,3-a][1,4]diazepin-8-yl trifluoromethanesulfonate (for a preparation see Intermediate 3) (500 mg) potassium carbonate (638 mg), 3-formylphenylboronic acid (166 mg) and bis(triphenylphosphine)palladium(II) chloride (64.8 mg) were added to a 20 ml microwave vial. Ethanol (9 ml) and toluene (9 ml) were added to the vial and the reaction mixture was heated at 120° C. for 20 min (microwave). The reaction mixture was filtered through Celite™ and the filter bed was washed with ethanol. The solvent was evaporated and the residue was chromatographed (0-10% methanol:DCM) to give (S)-2-(6-(4-chlorophenyl)-8-(3-formylphenyl)-1-methyl-4H-benzo[f][1,2,4]triazolo[4,3-a][1,4]diazepin-4-yl)-N-ethylacetamide as a light brown solid (287 mg). LCMS (formate): MH+ 498/500, RT 0.99 min

Intermediate 6

(S)-2-(6-(4-Chlorophenyl)-8-(4-formylphenyl)-1-methyl-4H-benzo[f][1,2,4]triazolo[4,3-a][1,4]diazepin-4-yl)-N-ethylacetamide

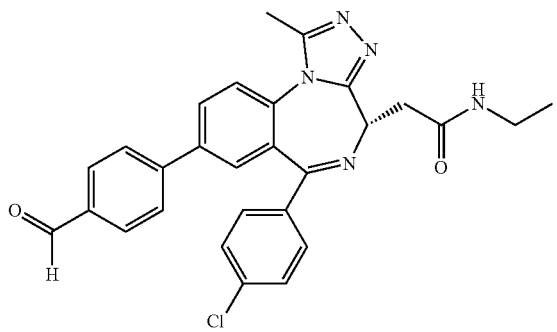 [SMILES: CCNC(=O)C[C@@H]1N=C(c2ccc(Cl)cc2)c2cc(-c3ccc(C=O)cc3)ccc2-n2c(C)nnc21]

(S)-6-(4-Chlorophenyl)-4-(2-(ethylamino)-2-oxoethyl)-1-methyl-4H-benzo[f][1,2,4]triazolo[4,3-a][1,4]diazepin-8-yl trifluoromethanesulfonate (for a preparation see intermediate 3) (500 mg), 4-formylphenylboronic acid (166 mg), potassium carbonate (638 mg) and bis(triphenylphosphine)palladium(II) chloride (64.8 mg) were added to a 20 ml microwave vial. Ethanol (9 ml) and toluene (9 ml) were added to the vial. The reaction mixture was heated in a microwave at 120° C. for 20 min. The reaction mixture was filtered through Celite™ and the filter bed was washed with ethanol. The solvent was evaporated, and the residue was chromatographed (0-5% methanol:DCM) to give (S)-2-(6-(4-chlorophenyl)-8-(4-formylphenyl)-1-methyl-4H-benzo[f][1,2,4]triazolo[4,3-a][1,4]diazepin-4-yl)-N-ethylacetamide (327 mg) as a brown solid. LCMS (formate): MH+ 498/500, RT 0.98 min

Intermediate 7

(S)-2-(6-(4-Chlorophenyl)-8-cyano-1-methyl-4H-benzo[f][1,2,4]triazolo[4,3-a][1,4]diazepin-4-yl)-N-ethylacetamide

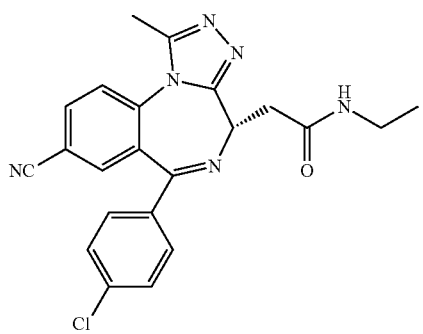

DMF (4 ml) was de-gassed for 20 min. (S)-6-(4-Chlorophenyl)-4-(2-(ethylamino)-2-oxoethyl)-1-methyl-4H-benzo[f][1,2,4]triazolo[4,3-a][1,4]diazepin-8-yl trifluoromethanesulfonate for a preparation see Intermediate 3) (250 mg) zinc cyanide (54.2 mg) and tetrakis(triphenylphosphine)palladium(0) (53.3 mg) were added to a 2-5 ml microwave vial. The de-gassed DMF (4 ml) was added and the reaction heated at 140° C. for 2 h (microwave). The reaction mixture was filtered through Celite™ and the filter bed was washed with ethyl acetate. The filtrate was partitioned between ethyl acetate and water. The organic phase was washed with water (2×10 ml) and brine (10 ml). The organics were dried and the solvent was evaporated. The residue was chromatographed (0-5% methanol:DCM) and triturated with diethyl ether to give (S)-2-(6-(4-chlorophenyl)-8-cyano-1-methyl-4H-benzo[f][1,2,4]triazolo[4,3-a][1,4]diazepin-4-yl)-N-ethylacetamide (73.5 mg) as a white solid.

LCMS (formate): MH+ 419/421, RT 0.86 min

Intermediate 8

Ethyl [(4S)-6-(4-chlorophenyl)-8-hydroxy-1-methyl-4H-[1,2,4]triazolo[4,3-a][1,4]benzodiazepin-4-yl]acetate

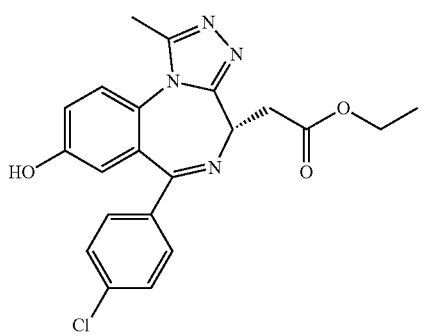 [SMILES: CCNC(=O)C[C@@H]1N=C(c2ccc(Cl)cc2)c2cc(C#N)ccc2-n2c(C)nnc21]

[(4S)-6-(4-Chlorophenyl)-1-methyl-8-(methyloxy)-4H-[1,2,4]triazolo[4,3-a][1,4]benzodiazepin-4-yl]acetic acid (1.2 g) was dissolved in DCM (30 ml) and cooled to −78° C. A solution of boron tribromide (2.86 ml) in DCM (6 ml) was added to the mixture slowly. The reaction was stirred at −78° C. for 25 min and then at room temperature overnight. The reaction was quenched by dropwise addition of a solution of ethanol (6 ml) in DCM (30 ml). The solvent was evaporated and the residue dissolved in ethanol (20 ml). Concentrated sulphuric acid (1 ml) was added and the mixture was refluxed for 3.5 h. The solvent was evaporated and the residue was dissolved in ethyl acetate (45 ml). The solution was washed with water (2×30 ml) then brine (10 ml), the organic phase dried and the solvent evaporated to give Ethyl [(4S)-6-(4-chlorophenyl)-8-hydroxy-1-methyl-4H-[1,2,4]triazolo[4,3-a][1,4]benzodiazepin-4-yl]acetate (519 mg) as a yellow solid, which was used without further purification in the subsequent reaction. LCMS (formate): MH$^+$ 411/413, RT 0.90 min

Example 1

2-[(4S)-6-(4-Chlorophenyl)-1-methyl-8-phenyl-4H-[1,2,4]triazolo[4,3-a][1,4]benzodiazepin-4-yl]-N-ethylacetamide

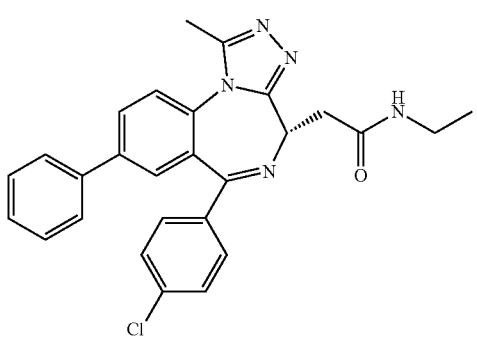 [SMILES: CCNC(=O)C[C@@H]1N=C(c2ccc(Cl)cc2)c2cc(-c3ccccc3)ccc2-n2c(C)nnc21]

[(4S)-6-(4-Chlorophenyl)-1-methyl-8-phenyl-4H-[1,2,4]triazolo[4,3-a][1,4]benzodiazepin-4-yl]acetic acid (for a preparation see Intermediate 1) (29 mg) was dissolved in DMF (2 ml). DIPEA (23 μl), HATU (29.9 mg) and ethylamine hydrochloride (10.68 mg) were added to the reaction mixture. The reaction was stirred at room temperature overnight. The mixture was dissolved in ethyl acetate (10 ml) and washed with saturated hydrogen carbonate solution (5 ml). The organic phase was washed with water (5 ml) and brine (5 ml). The organic layer was dried and the solvent evaporated. The residue was chromatographed (0-5% methanol:DCM) and then further purified by MDAP (formate modifier) to give 2-[(4S)-6-(4-chlorophenyl)-1-methyl-8-phenyl-4H-[1,2,4]triazolo[4,3-a][1,4]benzodiazepin-4-yl]-N-ethylacetamide (7.5 mg) as a white oil. LCMS (formate): MH$^+$ 470/472, RT 1.10 min

Example 2 ethyl [(4S)-6-(4-Chlorophenyl)-1-methyl-8-(4-pyridinyl)-4H-[1,2,4]triazolo[4,3-a][1,4]benzodiazepin-4-yl]acetate

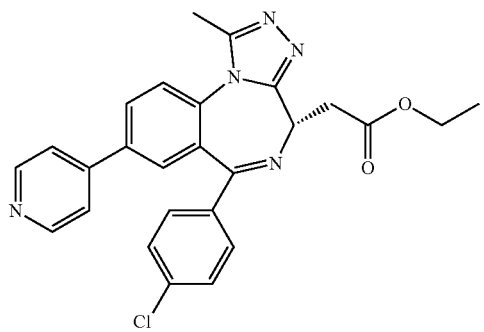 [SMILES: CCOC(=O)C[C@@H]1N=C(c2ccc(Cl)cc2)c2cc(-c3ccncc3)ccc2-n2c(C)nnc21]

Sodium carbonate (66.3 mg), 4-pyridinylboronic acid (22.5 mg) and bis(triphenylphosphine)palladium(II) chloride (19.1 mg) were added to a 2-5 ml microwave vial. A solution of ethyl ((4S)-6-(4-chlorophenyl)-1-methyl-8-{[(trifluoromethyl)sulfonyl]oxy}-4H-[1,2,4]triazolo[4,3-a][1,4]benzodiazepin-4-yl)acetate (for a preparation see intermediate 2) (147.5 mg) in DME (3 ml) and water (1 ml) was added to the microwave vial. The reaction mixture was heated at 120° C. for 90 min (microwave). Ethyl acetate (2 ml) was added and the water layer was separated and acidified with glacial acetic acid. The aqueous was extracted with ethyl acetate (3×5 ml), the organic fractions dried and the solvent evaporated. The residue was chromatographed (0-10% methanol:DCM) and then further purified by MDAP (formate modifier) to give ethyl [(4S)-6-(4-chlorophenyl)-1-methyl-8-(4-pyridinyl)-4H-[1,2,4]triazolo[4,3-a][1,4]benzodiazepin-4-yl]acetate as a white solid (5.5 mg).

LCMS (formate): MH$^+$ 472/474, RT 0.79 min

Example 3

2-{(4S)-6-(4-Chlorophenyl)-1-methyl-8-[4-(methyloxy)phenyl]-4H-[1,2,4]triazolo[4,3-a][1,4]benzodiazepin-4-yl}-N-ethylacetamide

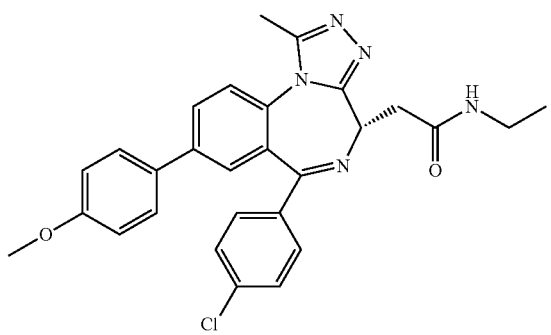 [SMILES: CCNC(=O)C[C@@H]1N=C(c2ccc(Cl)cc2)c2cc(-c3ccc(OC)cc3)ccc2-n2c(C)nnc21]

4-Methoxybenzeneboronic acid (50.5 mg), sodium carbonate (64.5 mg) and bis(triphenylphosphine)palladium(II) chloride (19.4 mg) were added to a 2-5 ml microwave vial. A solution of (4S)-6-(4-chlorophenyl)-4-[2-(ethylamino)-2-oxoethyl]-1-methyl-4H-[1,2,4]triazolo[4,3-a][1,4]benzodiazepin-8-yl trifluoromethanesulfonate (for a preparation see Intermediate 3) (150 mg) in DME (3 ml) and water (1 ml) was added and the reaction mixture was heated at 120° C. for 20 min (microwave). The reaction mixture was partitioned between ethyl acetate (10 ml) and water (10 ml). The organic phase was separated, washed with water (10 ml) and brine (10 ml). The organic phase was dried and the solvent was evaporated. The residue was chromatographed (0-5% methanol: DCM) to give 2-{(4S)-6-(4-chlorophenyl)-1-methyl-8-[4-(methyloxy)phenyl]-4H-[1,2,4]triazolo[4,3-a][1,4]benzodiazepin-4-yl}-N-ethylacetamide as a light brown solid (84 mg). LCMS (formate): MH+ 500/502, RT 1.08 min

Example 4

2-[(4S)-6-(4-Chlorophenyl)-1-methyl-8-(1H-pyrazol-5-yl)-4H-[1,2,4]triazolo[4,3-a][1,4]benzodiazepin-4-yl]-N-ethylacetamide

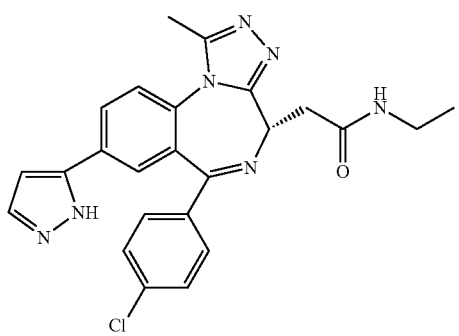 [SMILES: CCNC(=O)C[C@@H]1N=C(c2ccc(Cl)cc2)c2cc(-c3ccn[nH]3)ccc2-n2c(C)nnc21]

Sodium carbonate (43.0 mg), 1H-pyrazole-5-boronic acid (24.8 mg) and bis(triphenylphosphine)palladium(II) chloride (13.0 mg) were added to a 2-5 ml microwave vial. A solution of (4S)-6-(4-chlorophenyl)-4-[2-(ethylamino)-2-oxoethyl]-1-methyl-4H-[1,2,4]triazolo[4,3-a][1,4]benzodiazepin-8-yl trifluoromethanesulfonate (for a preparation see intermediate 3) (100 mg) in DME (3 ml) and water (1 ml) was added. The reaction mixture was heated at 120° C. for 30 min (microwave). Ethyl acetate (2 ml) was added and the water layer was separated. The organic phase was dried and the solvent evaporated. The residue was chromatographed (0-5% methanol: DCM) and the product further purified by MDAP (formate modifier). The resulting gum was loaded on a 1 g SCX-2 column and washed with ammonia in methanol (2M) to give 2-[(4S)-6-(4-chlorophenyl)-1-methyl-8-(1H-pyrazol-5-yl)-4H-[1,2,4]triazolo[4,3-a][1,4]benzodiazepin-4-yl]-N-ethylacetamide as a brown oil (15.6 mg).

LCMS (formate): MH+ 460/462, RT 0.80 min

Example 5

2-[(4S)-6-(4-Chlorophenyl)-1-methyl-8-(1H-pyrazol-4-yl)-4H-[1,2,4]triazolo[4,3-a][1,4]benzodiazepin-4-yl]-N-ethylacetamide

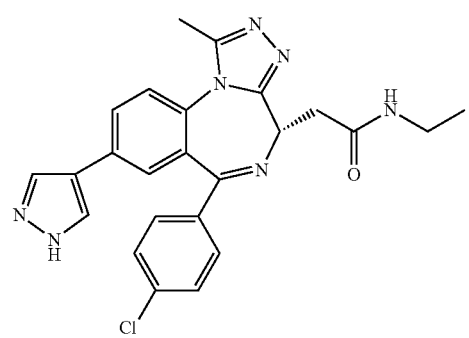 [SMILES: CCNC(=O)C[C@@H]1N=C(c2ccc(Cl)cc2)c2cc(-c3cn[nH]c3)ccc2-n2c(C)nnc21]

Sodium carbonate (43.0 mg), 1H-pyrazole-4-boronic acid (24.8 mg) and bis(triphenylphosphine)palladium(II) chloride (13.0 mg) were added to a 2-5 ml microwave vial. A solution of (4S)-6-(4-chlorophenyl)-4-[2-(ethylamino)-2-oxoethyl]-1-methyl-4H-[1,2,4]triazolo[4,3-a][1,4]benzodiazepin-8-yl trifluoromethanesulfonate (100 mg, intermediate 3) in DME (3 ml) and water (1 ml) was added. The reaction mixture was heated at 120° C. for 30 min (microwave). Ethyl acetate (2 ml) was added and the water layer was separated. The organic layer was dried and the solvent evaporated. The residue was purified by MDAP (formate modifier). The product was loaded on a 1 g SCX-2 column in methanol and eluted with ammonia in methanol (2M) to give 2-[(4S)-6-(4-chlorophenyl)-1-methyl-8-(1H-pyrazol-4-yl)-4H-[1,2,4]triazolo[4,3-a][1,4]benzodiazepin-4-yl]-N-ethylacetamide as a white oil (6.1 mg).

LCMS (formate): MH+ 460/462, RT 0.79 min

Example 6

2-[(4S)-6-(4-Chlorophenyl)-1-methyl-8-(2-methylphenyl)-4H-[1,2,4]triazolo[4,3-a][1,4]benzodiazepin-4-yl]-N-ethylacetamide

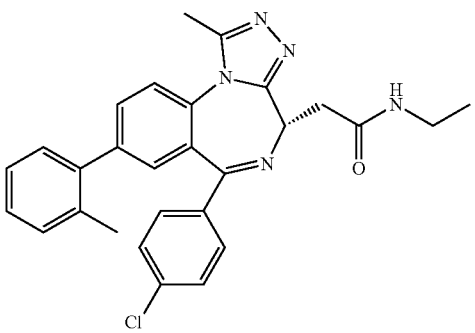 [SMILES: CCNC(=O)C[C@@H]1N=C(c2ccc(Cl)cc2)c2cc(-c3ccccc3C)ccc2-n2c(C)nnc21]

o-Tolylboronic acid (30.1 mg), sodium carbonate (43.0 mg) and bis(triphenylphosphine)palladium(II) chloride (12.95 mg) were added to a 2-5 ml microwave vial. A solution of (4S)-6-(4-chlorophenyl)-4-[2-(ethylamino)-2-oxoethyl]-1-methyl-4H-[1,2,4]triazolo[4,3-a][1,4]benzodiazepin-8-yl trifluoromethanesulfonate (for a preparation see intermediate 3) (100 mg) in DME (3 ml) and water (1 ml) was added and the reaction mixture was heated at 120° C. for 20 min (microwave) and then at 120° C. for a further 30 min (microwave). Bis(triphenylphosphine)palladium(II) chloride (12.7 mg) was added and the reaction mixture was heated at 120° C. for 30 min (microwave). The reaction mixture was partitioned between ethyl acetate (10 ml) and water (10 ml). The organic phase was separated and washed with water (10 ml) and brine (10 ml), dried and the solvent evaporated. The residue was chromatographed (0-5% methanol:DCM). The resulting mixture was repurified by MDAP (formate modifier) to give 2-[(4S)-6-(4-chlorophenyl)-1-methyl-8-(2-methylphenyl)-4H-[1,2,4]triazolo[4,3-a][1,4]benzodiazepin-4-yl]-N-ethylacetamide as a white oil (16.8 mg). LCMS (formate): MH+ 484/486, RT 1.14 min

Example 7

2-[(4S)-6-(4-Chlorophenyl)-1-methyl-8-(3-pyridinyl)-4H-[1,2,4]triazolo[4,3-a][1,4]benzodiazepin-4-yl]-N-ethylacetamide

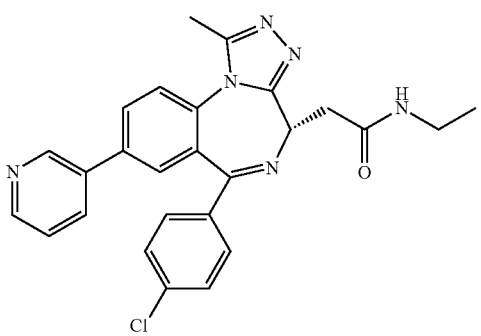 [SMILES: CCNC(=O)C[C@@H]1N=C(c2ccc(Cl)cc2)c2cc(-c3cccnc3)ccc2-n2c(C)nnc21]

3-Pyridinylboronic acid (27.2 mg), sodium carbonate (43.0 mg) and bis(triphenylphosphine)palladium(II) chloride (12.95 mg) were added to a 2-5 ml microwave vial. A solution of (4S)-6-(4-chlorophenyl)-4-[2-(ethylamino)-2-oxoethyl]-1-methyl-4H-[1,2,4]triazolo[4,3-a][1,4]benzodiazepin-8-yl trifluoromethanesulfonate (for a preparation see Intermediate 3) (100 mg) in DME (3 ml) and water (1 ml) was added and the reaction mixture was heated at 120° C. for 20 min (microwave). The reaction mixture was partitioned between ethyl acetate (10 ml) and water (10 ml). The organic phase was separated, washed with water (10 ml) and brine (10 ml). The organic phase was dried and the solvent evaporated. The residue was chromatographed (0-10% methanol:DCM) product was further purified by MDAP (formate modifier) to give 2-[(4S)-6-(4-chlorophenyl)-1-methyl-8-(3-pyridinyl)-4H-[1,2,4]triazolo[4,3-a][1,4]benzodiazepin-4-yl]-N-ethylacetamide as a white oil (11.9 mg).

LCMS (formate): MH+ 471/473, RT 0.73 min

Example 8

(S)-2-(6-(4-Chlorophenyl)-8-(3-methoxyphenyl)-1-methyl-4H-benzo[f][1,2,4]triazolo[4,3-a][1,4]diazepin-4-yl)-N-ethylacetamide

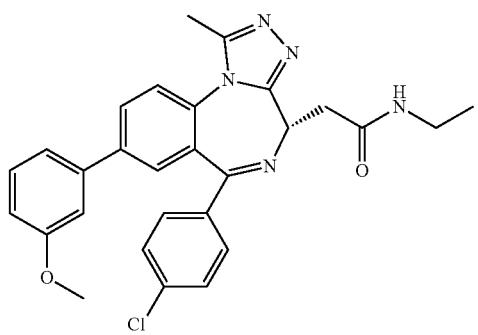 [SMILES: CCNC(=O)C[C@@H]1N=C(c2ccc(Cl)cc2)c2cc(-c3cccc(OC)c3)ccc2-n2c(C)nnc21]

(S)-6-(4-Chlorophenyl)-4-(2-(ethylamino)-2-oxoethyl)-1-methyl-4H-benzo[f][1,2,4]triazolo[4,3-a][1,4]diazepin-8-yl trifluoromethanesulfonate (for a preparation see Intermediate 3) (100 mg), bis(triphenylphosphine)palladium(II) chloride (12.95 mg), potassium carbonate (128 mg) and 3-methoxyphenylboronic acid (33.6 mg) were added to a 2-5 ml microwave vial. Toluene (2 ml) and ethanol (2 ml) were added to the vial and the reaction mixture was heated at 120° C. for 20 min (microwave). The reaction mixture was filtered through Celite™ and the filter bed was washed with ethanol. The solvent was evaporated and the residue was chromatographed (0-5% methanol:DCM), triturated with diethyl ether and dried in a vacuum dessicator at 40° C. overnight to give (S)-2-(6-(4-chlorophenyl)-8-(3-methoxyphenyl)-1-methyl- 4H-benzo[f][1,2,4]triazolo[4,3-a][1,4]diazepin-4-yl)-N-ethylacetamide as a cream solid (59.6 mg). LCMS (formate): MH+ 500/502, RT 1.09 min

Example 9

(S)-2-(6-(4-Chlorophenyl)-1-methyl-8-(pyridin-4-yl)-4H-benzo[f][1,2,4]triazolo[4,3-a][1,4]diazepin-4-yl)-N-ethylacetamide

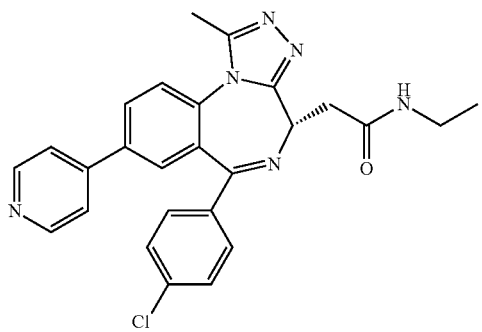 [SMILES: CCNC(=O)C[C@@H]1N=C(c2ccc(Cl)cc2)c2cc(-c3ccncc3)ccc2-n2c(C)nnc21]

(S)-6-(4-Chlorophenyl)-4-(2-(ethylamino)-2-oxoethyl)-1-methyl-4H-benzo[f][1,2,4]triazolo[4,3-a][1,4]diazepin-8-yl trifluoromethanesulfonate (for a preparation see Intermediate 3) (100 mg), bis(triphenylphosphine)palladium(II) chloride (12.95 mg), potassium carbonate (128 mg) and 4-pyridineboronic acid (27.2 mg) were added to a 2-5 ml microwave vial. Toluene (2 ml) and ethanol (2 ml) were added to the vial and the reaction mixture was heated at 120° C. for 20 min (microwave). The reaction mixture was filtered through Celite™ and the filter bed was washed with ethanol. The solvent was evaporated and the residue was chromatographed (0-5% methanol:DCM), triturated with diethyl ether and dried in a vacuum dessicator at 40° C. overnight to give the product as a cream solid. (S)-2-(6-(4-chlorophenyl)-1-methyl-8-(pyridin-4-yl)-4H-benzo[f][1,2,4]triazolo[4,3-a][1,4]diazepin-4-yl)-N-ethylacetamide (51.7 mg).
LCMS (formate): MH+ 471/473, RT 0.67 min

Example 10

(S)-2-(6-(4-Chlorophenyl)-1-methyl-8-(3-((4-methylpiperazin-1-yl)methyl)phenyl)-4H-benzo[f][1,2,4]triazolo[4,3-a][1,4]diazepin-4-yl)-N-ethylacetamide

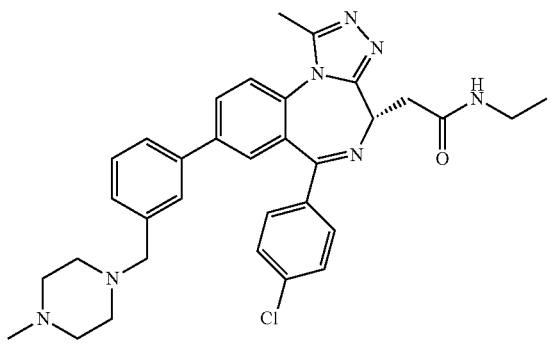 [SMILES: CCNC(=O)C[C@@H]1N=C(c2ccc(Cl)cc2)c2cc(-c3cccc(CN4CCN(C)CC4)c3)ccc2-n2c(C)nnc21]

(S)-2-(6-(4-Chlorophenyl)-8-(3-formylphenyl)-1-methyl-4H-benzo[f][1,2,4]triazolo[4,3-a][1,4]diazepin-4-yl)-N-ethylacetamide (for a preparation see Intermediate 5) (75 mg) was dissolved in DCM (5 ml). 1-methylpiperazine (25 µl) and acetic acid (8.62 µl) were added and the reaction mixture was stirred for 5 min. Sodium triacetoxyborohydride (160 mg) was added and the reaction mixture was stirred at room temperature, under nitrogen, overnight. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM), triturated with diethyl ether and dried in a vacuum dessicator at 40° C. over the weekend to give (S)-2-(6-(4-chlorophenyl)-1-methyl-8-(3-((4-methylpiperazin-1-yl)methyl)phenyl)-4H-benzo[f][1,2,4]triazolo[4,3-a][1,4]diazepin-4-yl)-N-ethylacetamide (49.2 mg) as a white solid. LCMS (formate): MH+ 582/584, RT 0.77 min

Example 11

(S)-2-(6-(4-Chlorophenyl)-8-(3-((ethylamino)methyl)phenyl)-1-methyl-4H-benzo[f][1,2,4]triazolo[4,3-a][1,4]diazepin-4-yl)-N-ethylacetamide

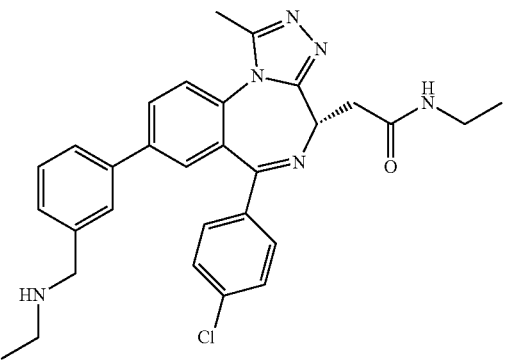 [SMILES: CCNCc1cccc(-c2ccc3c(c2)C(c2ccc(Cl)cc2)=N[C@@H](CC(=O)NCC)c2nnc(C)n2-3)c1]

(S)-2-(6-(4-Chlorophenyl)-8-(3-formylphenyl)-1-methyl-4H-benzo[f][1,2,4]triazolo[4,3-a][1,4]diazepin-4-yl)-N-ethylacetamide (for a preparation see Intermediate 5) (75 mg) was dissolved in DCM (5 ml). Ethylamine hydrochloride (18.42 mg) and acetic acid (8.62 µl) were added and the reaction mixture was stirred for 5 min. Sodium triacetoxyborohydride (160 mg) was added and the reaction mixture was stirred at room temperature, under nitrogen, overnight. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM) and triturated with diethyl ether. The solid was dried in a vacuum dessicator at 40° C. over the weekend to give (S)-2-(6-(4-chlorophenyl)-8-(3-((ethylamino)methyl)phenyl)-1-methyl-4H-benzo[f][1,2,4]triazolo[4,3-a][1,4]diazepin-4-yl)-N-ethylacetamide (52.4 mg) as a white solid. LCMS (formate): MH+ 527, RT 0.75 min

Example 12

(S)-2-(6-(4-Chlorophenyl)-1-methyl-8-(3-(pyrrolidin-1-ylmethyl)phenyl)-4H-benzo[f][1,2,4]triazolo[4,3-a][1,4]diazepin-4-yl)-N-ethylacetamide

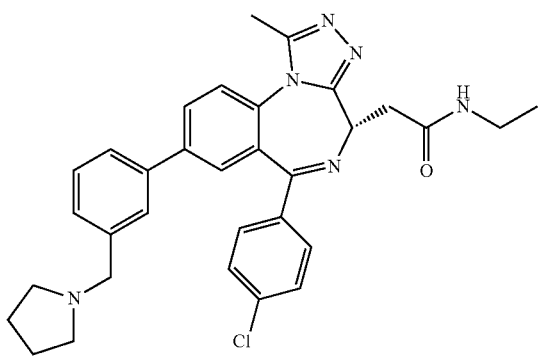 [SMILES: CCNC(=O)C[C@@H]1N=C(c2ccc(Cl)cc2)c2cc(-c3cccc(CN4CCCC4)c3)ccc2-n2c(C)nnc21]

(S)-2-(6-(4-Chlorophenyl)-8-(3-formylphenyl)-1-methyl-4H-benzo[f][1,2,4]triazolo[4,3-a][1,4]diazepin-4-yl)-N-ethylacetamide (for a preparation see Intermediate 5) (95 mg) was dissolved in DCM (5 ml). Pyrrolidine (24 µl) and acetic acid (8.62 µl) were added and the reaction mixture was stirred for 5 min. Sodium triacetoxyborohydride (202 mg) was added and the reaction mixture was stirred at room temperature, under nitrogen, overnight. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM), triturated with diethyl ether and dried in a vacuum dessicator at 40° C. over the weekend to give (S)-2-(6-(4-chlorophenyl)-1-methyl-8-(3-(pyrrolidin-1-ylmethyl)phenyl)-4H-benzo[f][1,2,4]triazolo[4,3-a][1,4]diazepin-4-yl)-N-ethylacetamide (71.7 mg) as a white solid. LCMS (formate): MH+ 553/555, RT 0.76 min

Example 13

(S)-2-(6-(4-Chlorophenyl)-1-methyl-8-(4-(pyrrolidin-1-ylmethyl)phenyl)-4H-benzo[f][1,2,4]triazolo[4,3-a][1,4]diazepin-4-yl)-N-ethylacetamide

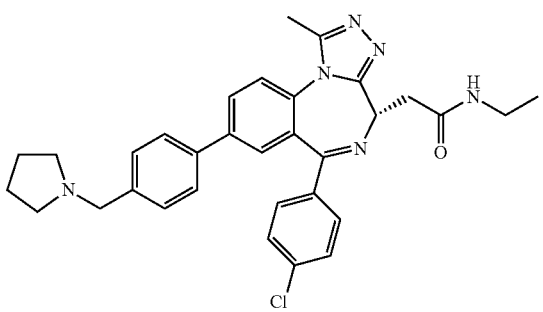 [SMILES: CCNC(=O)C[C@@H]1N=C(c2ccc(Cl)cc2)c2cc(-c3ccc(CN4CCCC4)cc3)ccc2-n2c(C)nnc21]

(S)-2-(6-(4-Chlorophenyl)-8-(4-formylphenyl)-1-methyl-4H-benzo[f][1,2,4]triazolo[4,3-a][1,4]diazepin-4-yl)-N-ethylacetamide (for a preparation see Intermediate 6) (75 mg) was dissolved in DCM (5 mL). Pyrrolidine (19 µl) and acetic acid (8.62 µl) were added and the reaction mixture was stirred for 5 min. Sodium triacetoxyborohydride (160 mg) was added and the reaction mixture was stirred at room temperature, under nitrogen, overnight. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM), triturated with diethyl ether and dried in a vacuum dessicator at 40° C. overnight to give (S)-2-(6-(4-chlorophenyl)-1-methyl-8-(4-(pyrrolidin-1-ylmethyl)phenyl)-4H-benzo[f][1,2,4]triazolo[4,3-a][1,4]diazepin-4-yl)-N-ethylacetamide (59.2 mg) as a white solid.

LCMS (formate): MH+ 553, RT 0.69 min

NMR (D6-DMSO): δH 8.25 (1H, t), 8.10 (1H, dd), 7.94 (1H, d), 7.65 (2H, d), 7.62 (1H, d), 7.55 (2H, d), 7.49 (2H, d), 7.40 (2H, d), 4.55 (1H, m), 3.62 (2H, bs), 3.29-3.07 (4H, m), 2.61 (3H, s), 2.45 (4H, bs), 1.70 (4H, bs), 1.07 (3H, t).

Example 14

(S)-2-(6-(4-Chlorophenyl)-1-methyl-8-(4-((4-methylpiperazin-1-yl)methyl)phenyl)-4H-benzo[f][1,2,4]triazolo[4,3-a][1,4]diazepin-4-yl)-N-ethylacetamide

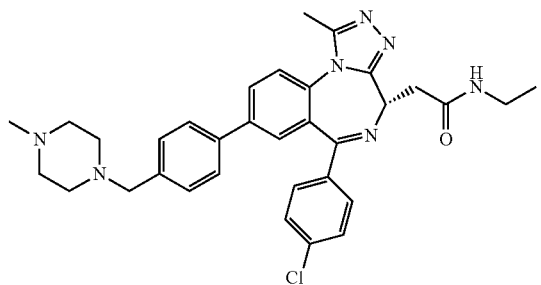 [SMILES: CCNC(=O)C[C@@H]1N=C(c2ccc(Cl)cc2)c2cc(-c3ccc(CN4CCN(C)CC4)cc3)ccc2-n2c(C)nnc21]

(S)-2-(6-(4-Chlorophenyl)-8-(4-formylphenyl)-1-methyl-4H-benzo[f][1,2,4]triazolo[4,3-a][1,4]diazepin-4-yl)-N-ethylacetamide (for a preparation see Intermediate 6) (90 mg) was dissolved in DCM (5 ml). 1-Methylpiperazine (30 µl) and acetic acid (10.35 µl) were added and the reaction mixture was stirred for 5 min. Sodium triacetoxyborohydride (192 mg) was added and the reaction mixture was stirred at room temperature, under nitrogen, over the weekend. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM), triturated with diethyl ether and dried in a vacuum dessicator at 40° C. overnight to give (S)-2-(6-(4-chlorophenyl)-1-methyl-8-(4-((4-methylpiperazin-1-yl)methyl)phenyl)-4H- benzo[f][1,2,4]triazolo[4,3-a][1,4]diazepin-4-yl)-N-ethylacetamide (66.5 mg) as a white solid. LCMS (formate): MH+ 582, RT 0.65 min Example 15

(S)-2-(6-(4-Chlorophenyl)-8-(4-((ethylamino)methyl)phenyl)-1-methyl-4H-benzo[f][1,2,4]triazolo[4,3-a][1,4]diazepin-4-yl)-N-ethylacetamide

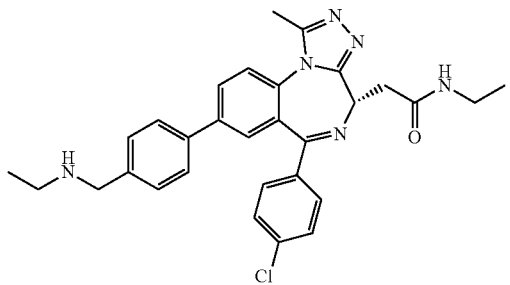 [SMILES: CCNCc1ccc(-c2ccc3c(c2)C(c2ccc(Cl)cc2)=N[C@@H](CC(=O)NCC)c2nnc(C)n2-3)cc1]

(S)-2-(6-(4-Chlorophenyl)-8-(4-formylphenyl)-1-methyl-4H-benzo[f][1,2,4]triazolo[4,3-a][1,4]diazepin-4-yl)-N-ethylacetamide (for a preparation see Intermediate 6) (75 mg) was dissolved in DCM (5 ml). Ethylamine hydrochloride (18.42 mg) and acetic acid (8.62 µl) were added and the reaction mixture was stirred for 5 min. Sodium triacetoxyborohydride (160 mg) was added and the reaction mixture was stirred at room temperature, under nitrogen, over the weekend. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM), triturated with diethyl ether and dried in a vacuum dessicator at 40° C. overnight to give (S)-2-(6-(4-chlorophenyl)-8-(4-((ethylamino)methyl)phenyl)-1-methyl-4H-benzo[f][1,2,4]triazolo[4,3-a][1,4]diazepin-4-yl)-N-ethylacetamide (28.7 mg) as a white solid. LCMS (formate): MH+ 527/529, RT 0.67 min Example 16

(S)-2-(6-(4-Chlorophenyl)-8-(4-((dimethylamino)methyl)phenyl)-1-methyl-4H-benzo[f][1,2,4]triazolo[4,3-a][1,4]diazepin-4-yl)-N-ethylacetamide

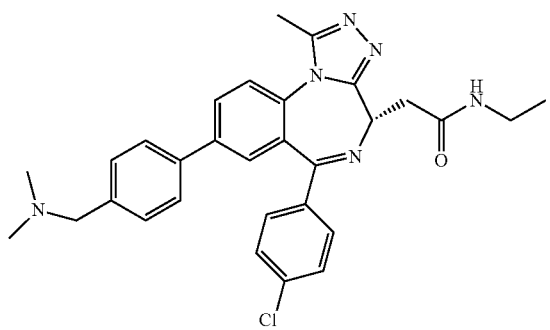 [SMILES: CCNC(=O)C[C@@H]1N=C(c2ccc(Cl)cc2)c2cc(-c3ccc(CN(C)C)cc3)ccc2-n2c(C)nnc21]

(S)-2-(6-(4-Chlorophenyl)-8-(4-formylphenyl)-1-methyl-4H-benzo[f][1,2,4]triazolo[4,3-a][1,4]diazepin-4-yl)-N-ethylacetamide (for a preparation see Intermediate 6) (75 mg) was dissolved in DCM (5 ml). Dimethylamine hydrochloride (18.42 mg) and acetic acid (8.62 µl) were added and the reaction mixture was stirred for 5 min. Sodium triacetoxyborohydride (160 mg) was added and the reaction mixture was stirred at room temperature, under nitrogen, for 5 h. Saturated sodium hydrogen carbonate solution (5 ml) was added and the reaction mixture was stirred for 10 min. The organic phase was separated and the saturated sodium hydrogen carbonate solution was extracted with DCM (10 ml). The DCM extracts were combined, dried and the solvent was evaporated. The residue was chromatographed (0-15% methanol:DCM), triturated with diethyl ether and dried in a vacuum dessicator overnight to give (S)-2-(6-(4-chlorophenyl)-8-(4-((dimethylamino)methyl)phenyl)-1-methyl-4H-benzo[f][1,2,4]triazolo[4,3-a][1,4]diazepin-4-yl)-N-ethylacetamide (48.2 mg) as a white solid. LCMS (formate): MH+ 527/529, RT 0.66 min Example 17

(S)-2-(6-(4-Chlorophenyl)-1-methyl-8-(2H-tetrazol-5-yl)-4H-benzo[f][1,2,4]triazolo[4,3-a][1,4]diazepin-4-yl)-N-ethylacetamide

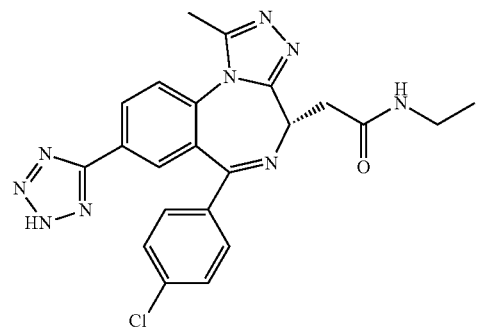 [SMILES: CCNC(=O)C[C@@H]1N=C(c2ccc(Cl)cc2)c2cc(-c3nn[nH]n3)ccc2-n2c(C)nnc21]

(S)-2-(6-(4-Chlorophenyl)-8-cyano-1-methyl-4H-benzo[f][1,2,4]triazolo[4,3-a][1,4]diazepin-4-yl)-N-ethylacetamide (for a preparation see Intermediate 7) (68.4 mg) was dissolved in DMF (5 ml). Triethylamine hydrochloride (45.0 mg) and sodium azide (21.23 mg) were added and the reaction mixture was heated at 100° C., under nitrogen, overnight. The temperature was raised to 120° C. and the reaction mixture was heated overnight. The reaction mixture was allowed to cool to room temperature, partitioned between ethyl acetate and water. The organic phase was washed with water (2×10 ml) and brine (10 ml). The aqueous layer was passed through a pre equilibrated Biotage 103 column. The organic content was eluted with methanol, the methanolic solution was evaporated and the residue was chromatographed (10-20% methanol:DCM). Trituration with diethyl ether gave (S)-2-(6-(4-chlorophenyl)-1-methyl-8-(2H-tetrazol-5-yl)-4H-benzo[f][1,2,4]triazolo[4,3-a][1,4]diazepin-4-yl)-N-ethylacetamide (25.6 mg) as a yellow solid. LCMS (formate): MH+ 462/464, RT 0.75 min Reference Compounds Experimental details of LC/MS methods A and B as referred to in the Reference compounds described below are as follows:

LC/MS (Method A) was conducted on a Supelcosil LCABZ+PLUS column (3 μm, 3.3 cm×4.6 mm ID) eluting with 0.1% HCO$_2$H and 0.01 M ammonium acetate in water (solvent A), and 95% acetonitrile and 0.05% HCO$_2$H in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give [M+H]$^+$ and [M+NH$_4$]$^+$ molecular ions] or electrospray negative ionisation [(ES−ve to give [M−H]− molecular ion] modes. Analytical data from this apparatus are given with the following format: [M+H]$^+$ or [M−H]$^−$.

LC/MS (Method B) was conducted on an Sunfire C18 column (30 mm×4.6 mm i.d. 3.5 μm packing diameter) at 30 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/HRMS: Analytical HPLC was conducted on a Uptisphere-hsc column (3 μm 33×3 mm id) eluting with 0.01 M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5 5% B at a flow rate of 1.3 mL/minute. The mass spectra (MS) were recorded on a micromass LCT mass spectrometer using electrospray positive ionisation [ES+ve to give MH$^+$ molecular ions] or electrospray negative ionisation [ES−ve to give (M−H)− molecular ions] modes.

Reference Compound A 2-methyl-6-(methyloxy)-4H-3,1-benzoxazin-4-one

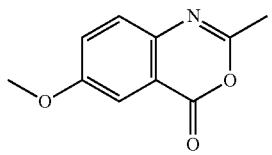

A solution of 5-methoxyanthranilic acid (Lancaster) (41.8 g, 0.25 mol) was refluxed in acetic anhydride (230 mL) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method A): m/z 192 [M+H]$^+$, Rt 1.69 min.

Reference Compound B

[2-amino-5-(methyloxy)phenyl](4-chlorophenyl)methanone

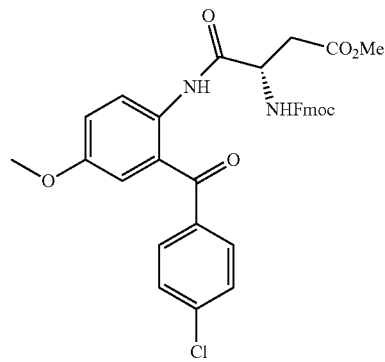

To a solution of 2-methyl-6-(methyloxy)-4H-3,1-benzoxazin-4-one (for a preparation see Reference compound A) (40.0 g, 0.21 mol) in a toluene/ether (2/1) mixture (760 mL) at 0° C. was added dropwise a solution of 4-chlorophenylmagnesium bromide (170 mL, 1M in Et$_2$O, 0.17 mol). The reaction mixture was allowed to warm to room temperature and stirred for 1 h before being quenched with 1N HCl (200 mL). The aqueous layer was extracted with EtOAc (3×150 mL) and the combined organics were washed with brine (100 mL), dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated to one-third in volume. The resulting solid was filtered and washed twice with ether before being suspended in EtOAc and neutralised with 1N NaOH. The aqueous layer was extracted with EtOAc (3×150 mL) and the combined organics were washed with brine (150 mL), dried over Na$_2$SO$_4$, filtered and concentrated under reduced pressure. The title compound was obtained as a yellow solid (39 g, 88% yield); LC/MS (Method A): m/z 262 [M+H]+, Rt 2.57 min.

Reference Compound C

Methyl N$^1$-[2-[(4-chlorophenyl)carbonyl]-4-(methyloxy)phenyl]-N$^2$-{[(9H-fluoren-9-ylmethyl)oxy]carbonyl}-L-α-asparaginate

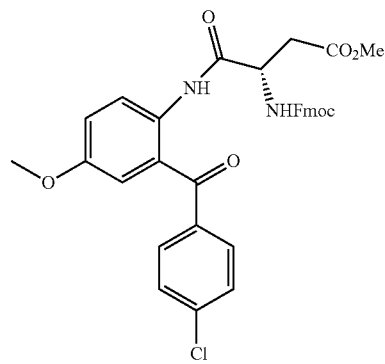

Methyl N-{[(9H-fluoren-9-ylmethyl)oxy]carbonyl}-L-α-aspartyl chloride (*Int. J. Peptide Protein Res.* 1992, 40, 13-18) (93 g, 0.24 mol) was dissolved in CHCl$_3$ (270 mL) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference Compound D

Methyl [(3S)-5-(4-chlorophenyl)-7-(methyloxy)-2-oxo-2,3-dihydro-1H-1,4-benzodiazepin-3-yl]acetate

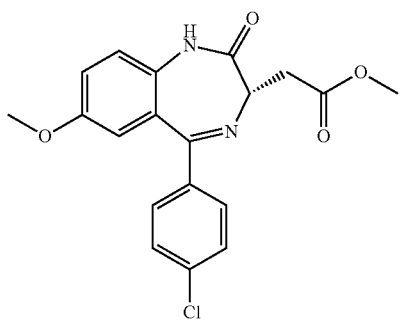

To a solution of Methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 mL) was added Et$_3$N (500 mL, 3.65 mol) and the resulting mixture was refluxed for 24 h before being concentrated. The resulting crude amine was dissolved in 1,2-DCE (1.5 L) and AcOH (104 mL, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product R$_f$=0.34 (DCM/MeOH:95/5).

HRMS (M+H)$^+$ calculated for C$_{19}$H$_{18}$$^{35}$ClN$_2$O$_4$ 373.0955; found 373.0957.

Reference Compound E

Methyl [(3S)-5-(4-chlorophenyl)-7-(methyloxy)-2-thioxo-2,3-dihydro-1H-1,4-benzodiazepin-3-yl]acetate

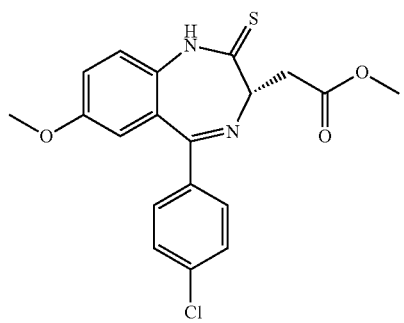

A suspension of P$_4$S$_{10}$ (36.1 g, 81.1 mmol) and Na$_2$CO$_3$ (8.6 g, 81.1 mmol) in 1,2-DCE (700 mL) at room temperature was stirred for 2 h before Methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. NaHCO$_3$ and brine. The organic layer was dried over Na$_2$SO$_4$, filtered and concentrated under reduced pressure. The crude product was purified by flash-chromatography on silica gel (DCM/MeOH:99/1) to afford the title compound (17.2 g, 98% yield) as a yellowish solid. LC/MS (Method A): m/z 389 [M($^{35}$Cl)+H]$^+$, Rt 2.64 min HRMS (M+H)$^+$ calculated for C$_{19}$H$_{18}$$^{35}$ClN$_2$O$_3$S 389.0727; found 389.0714.

Reference Compound F

Methyl [(3S)-2-[(1Z)-2-acetylhydrazino]-5-(4-chlorophenyl)-7-(methyloxy)-3H-1,4-benzodiazepin-3-yl]acetate

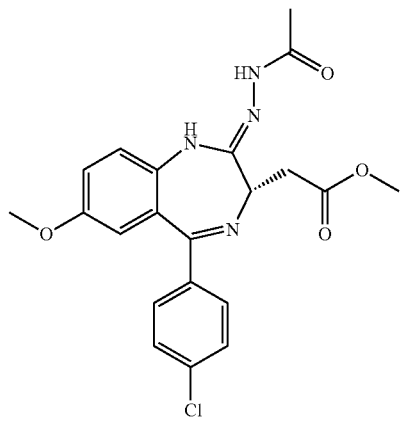

To a suspension of Methyl [(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 mL) at 0° C. was added hydrazine monohydrate (3.4 mL, 69.6 mmol) dropwise. The reaction mixture was stirred for 5 h between 5° C. and 15° C. before being cooled at 0° C. Et$_3$N (9.7 mL, 69.6 mmol) was then added slowly and acetyl chloride (7.95 mL, 69.6 mmol) was added dropwise. The mixture was then allowed to warm to room temperature for 16 h before being concentrated under reduced pressure. The crude product was dissolved in DCM and washed with water. The organic layer was dried over Na$_2$SO$_4$, filtered and concentrated in vacuo to give the crude title compound (9.7 g, 98% yield) which was used without further purification. R$_f$=0.49 (DCM/MeOH:90/10).

Reference Compound G

Methyl [(4S)-6-(4-chlorophenyl)-1-methyl-8-(methyloxy)-4H-[1,2,4]triazolo[4,3-a][1,4]benzodiazepin-4-yl]acetate

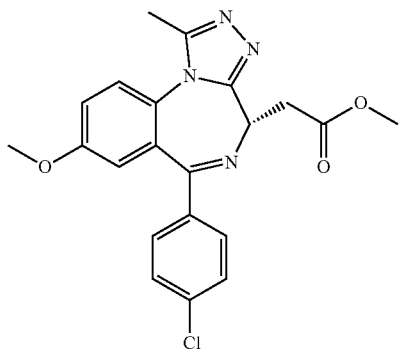

The crude Methyl [(3S)-2-[(1Z)-2-acetylhydrazino]-5-(4-chlorophenyl)-7-(methyloxy)-3H-1,4-benzodiazepin-3-yl]acetate (for a preparation see Reference compound F) (assumed 9.7 g) was suspended in THF (100 ml) and AcOH (60 mL) was added at room temperature. The reaction mixture was stirred at this temperature for 2 days before being concentrated under reduced pressure. The crude solid was triturated in i-Pr$_2$O and filtered to give the title compound (8.7 g, 91% over 3 steps) as an off-white solid.

HRMS (M+H)$^+$ calculated for C$_{21}$H$_{20}$ClN$_4$O$_3$ 411.1229; found 411.1245.

Reference Compound H

[(4S)-6-(4-Chlorophenyl)-1-methyl-8-(methyloxy)-4H-[1,2,4]triazolo[4,3-a][1,4]benzodiazepin-4-yl] acetic acid

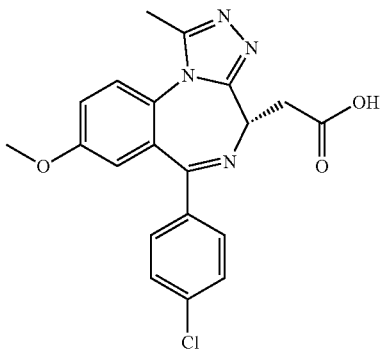 [SMILES: COc1ccc2c(c1)C(c1ccc(Cl)cc1)=N[C@@H](CC(=O)O)c1nnc(C)n1-2]

To a solution of Methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G) (7.4 g, 18.1 mmol) in THF (130 mL) at room temperature was added 1N NaOH (36.2 mL, 36.2 mmol). The reaction mixture was stirred at this temperature for 5 h before being quenched with 1N HCl (36.2 mL) and concentrated in vacuo. Water is then added and the aqueous layer was extracted with DCM (×3) and the combined organic layers were dried over Na$_2$SO$_4$, filtered and concentrated under reduced pressure to give the title compound (7 g, 98% yield) as a pale yellow solid.

Reference Compound I 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

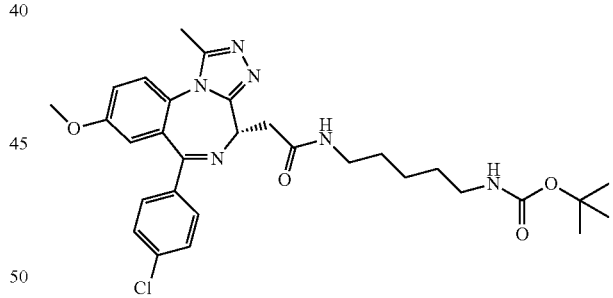

A mixture of [(4S)-6-(4-chlorophenyl)-1-methyl-8-(methyloxy)-4H-[1,2,4]triazolo[4,3-a][1,4]benzodiazepin-4-yl] acetic acid (for a preparation see Reference compound H) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method A): rt=3.04 min.

Reference Compound J

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

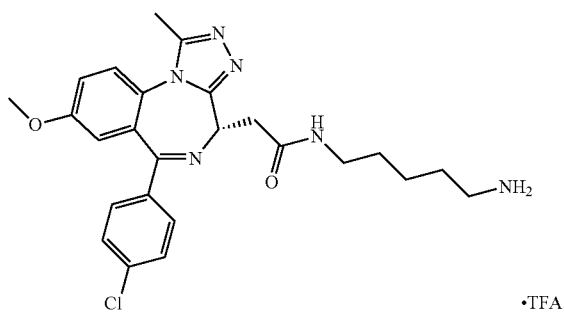 [SMILES: COc1ccc2c(c1)C(c1ccc(Cl)cc1)=N[C@@H](CC(=O)NCCCCCN)c1nnc(C)n1-2 ; "·TFA"]

To a solution of 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound I) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method A): rt=2.33 min.

HRMS (M+H)$^+$ calculated for $C_{25}H_{29}ClN_6O_2$ 481.2119; found 481.2162.

Reference Compound K

Mixture of 5- and 6-Isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide

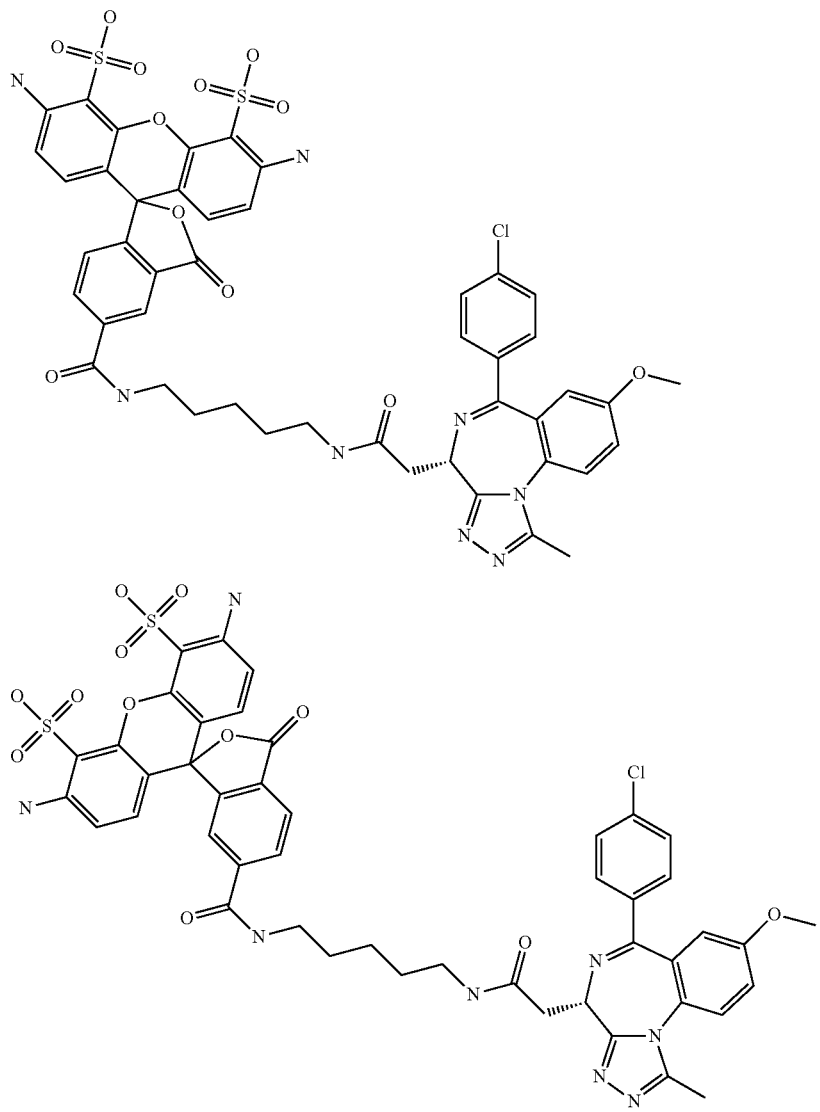 [SMILES: COc1ccc2c(c1)C(c1ccc(Cl)cc1)=N[C@@H](CC(=O)NCCCCCNC(=O)c1ccc3c(c1)C(=O)OC31c3ccc(N)c(S(=O)(=O)O)c3Oc3c1ccc(N)c3S(=O)(=O)O)c1nnc(C)n1-2 ; COc1ccc2c(c1)C(c1ccc(Cl)cc1)=N[C@@H](CC(=O)NCCCCCNC(=O)c1ccc3c(c1)C1(OC3=O)c3ccc(N)c(S(=O)(=O)O)c3Oc3c1ccc(N)c3S(=O)(=O)O)c1nnc(C)n1-2]

N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-Dimethylformamide (DMF) (300 μl) and added to Alexa Fluor 488 carboxylic acid succinimidyl ester (5 mg, 7.77 μmol, mixture of 5 and 6 isomers, available from Invitrogen, product number A-20100) in an Eppendorf centrifuge tube. Hunig's base (7.0 μl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown. LC/MS (Method B), MH+=999, rt=1.88 min.

Biological Test Methods

The compounds of formula (I) may be tested in the following assays.

Fluorescence Anisotropy Binding Assay

The binding of the compounds of formula (I) to Bromodomain 2, 3 and 4 can be assessed using an Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data are normalized to the mean of 16 high and 16 low control wells on each plate. A four parameter curve fit of the following form are then applied:

$$y=a+((b-a)/(1+(10^x/10^c)^d)$$

Where 'a' is the minimum, 'b' is the Hill slope, 'c' is the pIC50 and 'd' is the maximum.

Recombinant Human Bromodomains (Bromodomain 2 (1-473), Bromodomain 3 (1-435) and Bromodomain 4 (1-477)) are expressed in *E. coli* cells (in pET15b vector) with a six-His tag at the N-terminal. The His-tagged Bromodomain was extracted from *E. coli* cells using 0.1 mg/ml lysozyme and sonication. The Bromodomain are then purified by affinity chromatography on a HisTRAP HP column, eluting with a linear 10-500 mM Imidazole gradient, over 20 Cv. Further purification are completed by Superdex 200 prep grade size exclusion column. Purified protein are stored at −80 C in 20 mM HEPES pH 7.5 and 100 mM NaCl.

Protocol for Bromodomain 2:

All components are dissolved in buffer composition of 50 mM HEPES pH7.4, 150 mm NaCl and 0.5 mM CHAPS with final concentrations of Bromodomain 2, 75 nM, fluorescent ligand 5 nM. 10 μl of this reaction mixture are added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy are read in Envision (λex=485 nm, λEM=530 nm; Dichroic −505 nM).

Protocol for Bromodoamin 3:

All components are dissolved in buffer of composition 50 mM HEPES pH7.4, 150 mm NaCl and 0.5 mM CHAPS with final concentrations of Bromodomains 3 75 nM, fluorescent ligand 5 nM. 10 μl of this reaction mixture are added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy are read in Envision (λex=485 nm, λEM=530 nm; Dichroic −505 nM).

Protocol for Bromodomain 4:

All components are dissolved in buffer of composition 50 mM HEPES pH7.4, 150 mm NaCl and 0.5 mM CHAPS with final concentrations of Bromodomain 4 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy are read in Envision (λex=485 nm, λEM=530 nm; Dichroic −505 nM).

Time Resolved Fluorescence Resonance Energy Transfer (TR-FRET) Assay

The binding of the compounds of formula (I) to Bromodomains BRD2, BRD3 and BRD4 was assessed using a time resolved fluorescent resonance energy transfer binding assay, that measures the binding of an acetylated histone peptide to the bromodomain protein.

The bromodomain protein, histone peptide and a variable concentration of test compound are incubated together to reach thermodynamic equilibrium. The assay is configured such that in the absence of test compound the bromodomain and peptide are significantly bound (~30%) and in the presence of a sufficient concentration of a potent inhibitor this interaction is disrupted leading to a measurable drop in fluorescent resonance energy transfer.

Histone Peptide:

H-Ser-Gly-Arg-Gly-Lys(Ac)-Gly-Gly-Lys(Ac)-Gly-Leu-Gly-Lys(Ac)-Gly-Gly-Ala-Lys(Ac)-Arg-His-Gly-Ser-Gly-Ser-Lys(Biotin)-OH. 3TFA The protected peptide was assembled on a solid-phase synthesiser using preloaded Wang resin and utilising standard Fmoc synthesis protocols. The C-terminal lysine was protected by a hyper acid-labile group allowing for its selective removal at the end of the assembly and attachment of the biotin. The crude peptide was obtained after cleavage from the resin with a mixture of trifluoroacetic acid (TFA), triisopropylsilane and water (95:2.5:2.5) for 3 h at room temperature and was then purified using a C18 reverse-phase column utilising a 0.1% TFA-buffered water/acetonitrile gradient. The resulting fractions were analysed and fractions which were >95% pure by analytical HPLC and giving the correct mw (by MALDiTOF mass spectroscopy) were pooled and freeze dried. The final material was analysed by HPLC to confirm purity.

Protein Production:

Recombinant Human Bromodomains (BRD2 (1-473), BRD3 (1-435) and BRD4 (1-477)) were expressed in *E. coli* cells (in pET15b vector) with a six-His tag at the N-terminal. The His-tagged Bromodomain was extracted from *E. coli* cells using sonication and purified using a nickel sepharose 6FF column, the proteins were washed and then eluted with 50 mM Tris-Hcl pH8.0. 300 mM NaCl, 1 mM β-mercaptoethanol and 20 mM Imidazole. Further purification was performed by affinity chromatography on a HisTRAP HP column, eluting with a linear 0-500 mM sodium chloride gradient, over 20 column volumes. Final purification was completed by Superdex 200 prep grade size exclusion column. Purified protein was stored at −80 C in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3 and 4 Assays:

All assay components were dissolved in buffer composition of 50 mM HEPES pH7.4, 50 mM NaCl and 0.5 mM CHAPS. The final concentration of bromodomain proteins were 100 nM and the histone peptide was 300 nM, these components are premixed and allowed to equilibrate for 1 hour in the dark. 8 µl of this reaction mixture was added to all wells containing 50 nl of various concentrations of test compound or DMSO vehicle (0.5% final) in Greiner 384 well black low volume microtitre plates and incubated in dark for 60 mins at room temperature. 4l of detection mixture containing anti-6his XL665 labeled antibody and streptavidin labeled with europium cryptate was added to all wells and a further dark incubation of at least 30 mins was performed. Plates were then read on the Envision platereader, ($\lambda$ex=317 nm, donor $\lambda$EM=615 nm; acceptor $\lambda$EM=665 nm; Dichroic LANCE dual). Time resolved fluorescent intensity measurements were made at both emission wavelengths and the ratio of acceptor/donor was calculated and used for data analysis. All data was normalized to the mean of 16 high and 16 low control wells on each plate. A four parameter curve fit of the following form was then applied:

$$y=a+((b-a)/(1+(10^\wedge x/10^\wedge c)^\wedge d)$$

Where 'a' is the minimum, 'b' is the Hill slope, 'c' is the pIC50 and 'd' is the maximum.

Examples 1 and 3-17 were tested in one or more of the above assays and were found to have a pIC50≥5.5. Examples 1, 3-5 and 7-17 were tested in one or more of the above assays and were found to have a pIC50≥6.5.

LPS Stimulated Whole Blood Measuring TNFα Levels Assay

Activation of monocytic cells by agonists of toll-like receptors such as bacterial lipopolysaccharide (LPS) results in production of key inflammatory mediators including TNFα. Such pathways are widely considered to be central to the pathophysiology of a range of auto-immune and inflammatory disorders.

Compounds to be tested are diluted to give a range of appropriate concentrations and 1 ul of the dilution stocks is added to wells of a 96 plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and TNFα levels assayed by immunoassay (typically by MesoScale Discovery technology) either immediately or following storage at −20 degrees. Dose response curves for each compound is generated from the data and an IC50 value is calculated.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 ul of the diluted stocks is added to a 96 well plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and IL-6 levels assayed by immunoassay (typically by MesoScale Discovery technology) either immediately or following storage at −20 degrees. Concentration response curves for each compound was generated from the data and an $IC_{50}$ value was calculated Examples 1, 3, 4, 5 and 13 were tested in the above assay were found to have a pIC50≥5.5.

These data demonstrate that bromodomain inhibitors tested in the above whole blood assay inhibited the production of key inflammatory mediator IL-6.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds of formula (I) groups of eight Balb/c male mice are given a lethal dose of 15 mg/kg LPS by intraperitoneal injection. Ninety minutes later, animals are dosed intravenously with vehicle (20% cyclodextrin 1% ethanol in apyrogen water) or compound (10 mg/kg). The survival of animals is monitored at 4 days.

Oncology Cell Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 µl of culture media. All plates were placed at 5% $CO_2$, 37° C. overnight. The following day one plate was harvested with CellTiter-Glo (CTG, Promega #G7573) for a time equal to 0 (TO) measurement and compound (20 point titration from 14.7 uM to 7 µM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results are expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin−T0 value is determined by subtracting the T0 value (100%) from the Ymin value (%) determined from the fit of the concentration response curve. Values from the wells with no cells were subtracted from all samples for background correction.

All publications, including but not limited to patents and patent applications, cited in this specification are herein incorporated by reference as if each individual publication were specifically and individually indicated to be incorporated by reference herein as though fully set forth.

The invention claimed is:

1. A compound of formula (I) or a salt thereof

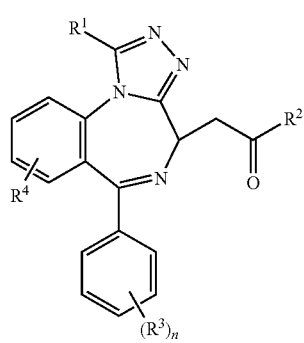

where
R$^1$ is C$_{1-3}$alkyl;
R$^2$ is —NR$^{2a}$R$^{2a'}$ or —OR$^{2b}$;
wherein one of R$^{2a}$ or R$^{2a'}$ is hydrogen, and R$^{2b}$ or the other of R$^{2a}$ or R$^{2a'}$ are selected from C$_{1-6}$alkyl, haloC$_{1-6}$alkyl, R$^{2c}$R$^{2'c}$N—C$_{2-6}$alkyl, R$^{2c}$O—C$_{2-6}$alkyl, carbocyclyl, carbocyclylC$_{1-4}$alkyl, heterocyclyl and heterocyclylC$_{1-4}$alkyl, wherein any of the carbocyclyl or heterocyclyl groups are optionally substituted by one or more groups selected from halogen, C$_{1-6}$alkyl, haloC$_{1-6}$alkyl, C$_{1-6}$alkoxy, haloC$_{1-6}$alkoxy, carbonyl, —CO-carbocyclyl, amino, hydroxyl and cyano, or two adjacent groups on any of the carbocyclyl or heterocyclyl groups together with the interconnecting atoms form a 5- or 6-membered ring which ring may contain 1 or 2 heteroatoms independently selected from O, S and N;
or R$^{2a}$ and R$^{2a'}$ together with the N-atom to which they are attached form a 5-, 6- or 7-membered ring which may optionally contain 1 or 2 heteroatoms independently selected from O, S and N; wherein the 5-, 6- or 7-membered ring may be further optionally substituted by C$_{1-6}$alkyl;
R$^{2c}$ and R$^{2'c}$ are independently hydrogen or C$_{1-6}$alkyl;
each R$^3$ is independently selected from hydrogen, hydroxy, halo, C$_{1-6}$alkyl, halo C$_{1-6}$alkyl, C$_{1-6}$alkoxy, halo C$_{1-6}$alkoxy, cyano, CF$_3$, —OCF$_3$, —COOR$^5$, —C$_{1-4}$alkylNR$^6$R$^7$ and —C$_{1-4}$alkylOH;
R$^4$ is an aromatic carbocyclic or aromatic heterocyclyl group;
wherein the aromatic carbocyclyl or heterocyclyl group is optionally substituted by one or more groups selected from halo, C$_{1-6}$alkyl, C$_{1-6}$alkoxy and a group C$_{1-4}$alkylNR$^6$R$^7$;
R$^5$ is C$_{1-3}$alkyl;
at each occurrence R$^6$ and R$^7$ are independently hydrogen, C$_{1-6}$alkyl or C(O)C$_{1-6}$alkyl, or R$^6$ and R$^7$ together with the N-atom to which they are attached form a 5-, 6- or 7-membered ring which optionally contains 1 or 2 further heteroatoms independently selected from O, S and N; wherein the 5-, 6- or 7-membered ring may be further optionally substituted by one or more C$_{1-6}$alkyl, —C(O)C$_{1-6}$alkyl, amino or hydroxyl groups; and
n is an integer 1 to 5.

2. A compound or a salt thereof according to claim 1, wherein R$^1$ is methyl.

3. A compound or a salt thereof according to claim 2, wherein R$^2$ is OR$^{2b}$.

4. A compound or a salt thereof according to claim 3, wherein R$^{2b}$ is C$_{1-6}$alkyl.

5. A compound or a salt thereof according to claim 4, wherein R$^{2b}$ is selected from methyl, ethyl, isopropyl and butyl.

6. A compound or a salt thereof according to claim 1, wherein R$^2$ is —NR$^{2a}$R$^{2a'}$.

7. A compound or a salt thereof according to claim 6, wherein R$^{2a}$ is hydrogen and R$^{2a'}$ is C$_{1-6}$alkyl.

8. A compound or a salt thereof according to claim 7, wherein R$^{2a'}$ is ethyl.

9. A compound or a salt thereof according to claim 6, wherein R$^{2a}$ is hydrogen and R$^{2a'}$ is R$^{2c}$R$^{2'c}$N—C$_{2-6}$alkyl.

10. A compound or a salt thereof according to claim 9 wherein R$^{2a'}$ selected from R$^{2c}$R$^{2'c}$N—CH$_2$CH$_2$—, R$^{2c}$R$^{2'c}$N—CH$_2$CH$_2$CH$_2$— and R$^{2c}$R$^{2'c}$N—CH$_2$CH$_2$CH$_2$CH$_2$—.

11. A compound or a salt thereof according to claim 10, wherein R$^{2c}$ and R$^{2'c}$ are selected from hydrogen and methyl.

12. A compound or a salt thereof according to claim 6, wherein R$^{2a}$ is hydrogen and R$^{2a'}$ is carbocyclyl.

13. A compound or a salt thereof according to claim 1 wherein R$^2$ is —NR$^{2a}$R$^{2a'}$, R$^{2a}$ is hydrogen, and R$^{2a'}$ is cyclopentyl or cyclohexyl, wherein each group is optionally substituted once by amino or hydroxyl.

14. A compound or a salt thereof according to claim 6, wherein R$^{2a}$ is hydrogen and R$^{2a'}$ is heterocyclyl.

15. A compound or a salt thereof according to claim 1 wherein R$^2$ is —NR$^{2a}$R$^{2a'}$, R$^{2a}$ is hydrogen, and R$^{2a'}$ is selected from pyrrolidinyl, piperidinyl, tetrahydrofuranyl and tetrahydropyran, wherein each group is optionally substituted by C$_{1-6}$alkyl.

16. A compound or a salt thereof according to claim 15, wherein R$^{2a'}$ is selected from:

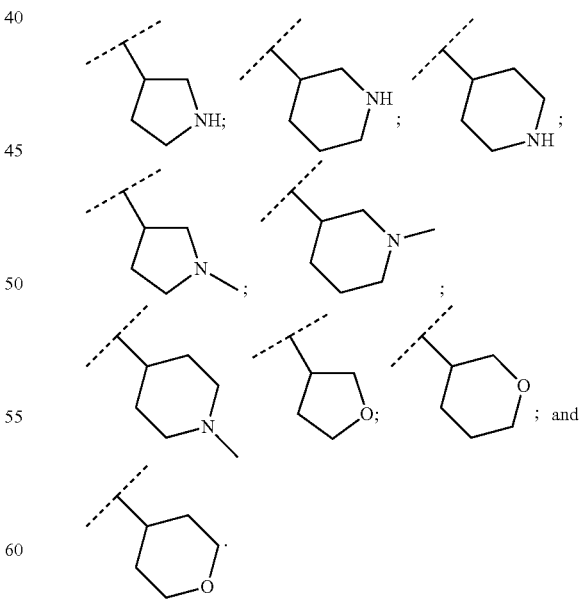

17. A compound or a salt thereof according to claim 6, wherein R$^{2a}$ is hydrogen and R$^{2a'}$ is heterocyclylC$_{1-4}$alkyl, wherein the heterocyclyl is optionally substituted once by amino, hydroxyl or methyl.

18. A compound or a salt thereof according to claim 17 wherein $R^{2a'}$ is selected from heterocyclyl-$CH_2$—, heterocyclyl-$CH_2CH_2$—, heterocyclyl-$CH_2CH_2CH_2$— and heterocyclyl-$CH_2CH_2CH_2CH_2$—, wherein the heterocyclyl is optionally substituted once by amino, hydroxyl or methyl.

19. A compound or a salt thereof according to claim 18, wherein heterocyclyl is selected from tetrahydrofuranyl, pyrrolidinyl, piperidinyl, tetrahydropyranyl, piperazinyl, morpholino and thiomorpholinodioxide, wherein each group is optionally substituted once by amino, hydroxyl or methyl.

20. A compound or a salt thereof according to claim 18, wherein heterocyclyl is selected from:

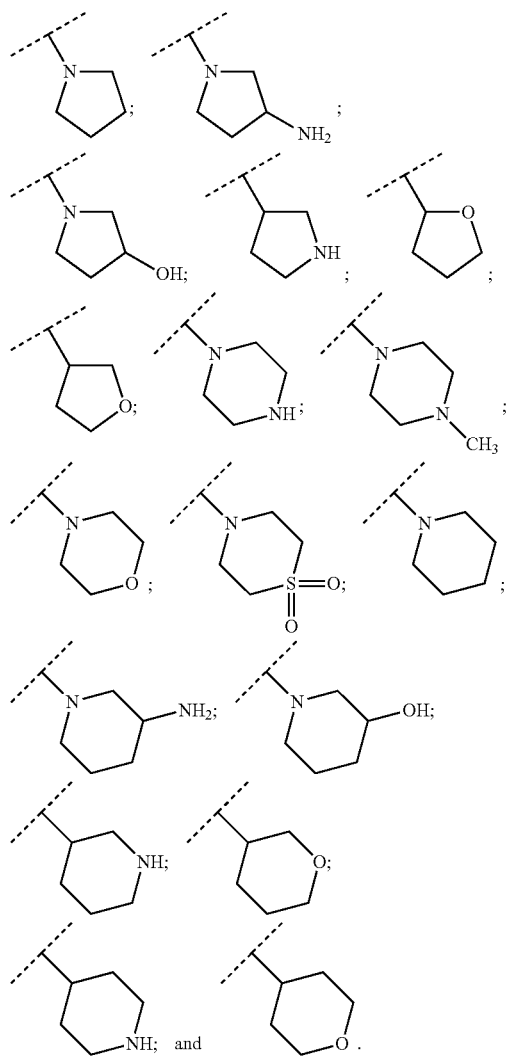

21. A compound or a salt thereof according claim 1, wherein n is 1.

22. A compound or a salt thereof according to claim 1, wherein $R^3$ is 3-fluoro, 4-chloro, 4-fluoro, 4-methoxy or 4-$CF_3$.

23. A compound or a salt thereof according to claim 22, wherein $R^3$ is 4-chloro.

24. A compound or a salt thereof according to claim 1, wherein $R^4$ is phenyl, pyridyl, imadolzolyl or pyrazolyl, such groups being optionally substituted by one or more groups selected from halo, $C_{1-6}$alkyl, $C_{1-6}$alkoxy or a group $C_{1-4}$alkyl$NR^6R^7$ in which $R^6$ is hydrogen and $R^7$ is hydrogen, $C_{1-6}$alkyl or $C(O)C_{1-6}$alkyl.

25. A compound or a salt thereof according to claim 24, wherein $R^4$ is selected from

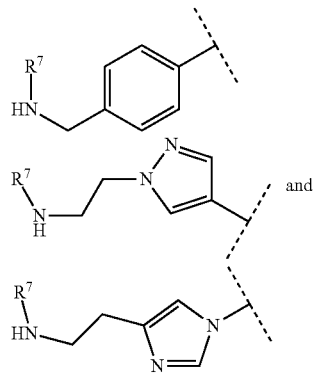

in which $R^7$ is hydrogen, methyl or C(O)Me.

26. A compound or a salt thereof according to claim 1 wherein $R^4$ is phenyl substituted by a group $C_{1-4}$alkyl$NR^6R^7$ in which $R^6$ and $R^7$ together with the N-atom to which they are attached form a pyrrolidinyl, piperazinyl, piperidinyl or morpholinyl ring said rings being optionally substituted by one or more $C_{1-6}$alkyl, —$C(O)C_{1-6}$alkyl, amino or hydroxyl groups.

27. A compound or a salt thereof according to claim 1 in which the $R^4$ group is at the 8 position of the benzodiazepine ring.

28. A compound which is selected from
2-[(4S)-6-(4-Chlorophenyl)-1-methyl-8-phenyl-4H-[1,2,4]triazolo[4,3-a][1,4]benzodiazepin-4-yl]-N-ethylacetamide;
Ethyl [(4S)-6-(4-Chlorophenyl)-1-methyl-8-(4-pyridinyl)-4H-[1,2,4]triazolo[4,3-a][1,4]benzodiazepin-4-yl] acetate;
2-{(4S)-6-(4-Chlorophenyl)-1-methyl-8-[4-(methyloxy)phenyl]-4H-[1,2,4]triazolo[4,3-a][1,4]benzodiazepin-4-yl}-N-ethylacetamide;
2-[(4S)-6-(4-Chlorophenyl)-1-methyl-8-(1H-pyrazol-5-yl)-4H-[1,2,4]triazolo[4,3-a][1,4]benzodiazepin-4-yl]-N-ethylacetamide;
2-[(4S)-6-(4-Chlorophenyl)-1-methyl-8-(1H-pyrazol-4-yl)-4H-[1,2,4]triazolo[4,3-a][1,4]benzodiazepin-4-yl]-N-ethylacetamide;
2-[(4S)-6-(4-Chlorophenyl)-1-methyl-8-(2-methylphenyl)-4H-[1,2,4]triazolo[4,3-a][1,4]benzodiazepin-4-yl]-N-ethylacetamide;
2-[(4S)-6-(4-Chlorophenyl)-1-methyl-8-(3-pyridinyl)-4H-[1,2,4]triazolo[4,3-a][1,4]benzodiazepin-4-yl]-N-ethylacetamide;
(S)-2-(6-(4-Chlorophenyl)-8-(3-methoxyphenyl)-1-methyl-4H-benzo[f][1,2,4]triazolo[4,3-a][1,4]diazepin-4-yl)-N-ethylacetamide;
(S)-2-(6-(4-Chlorophenyl)-1-methyl-8-(pyridin-4-yl)-4H-benzo[f][1,2,4]triazolo[4,3-a][1,4]diazepin-4-yl)-N-ethylacetamide;
(S)-2-(6-(4-Chlorophenyl)-1-methyl-8-(3-((4-methylpiperazin-1-yl)methyl)phenyl)-4H-benzo[f][1,2,4]triazolo[4,3-a][1,4]diazepin-4-yl)-N-ethylacetamide;
(S)-2-(6-(4-Chlorophenyl)-8-(3-((ethylamino)methyl)phenyl)-1-methyl-4H-benzo[f][1,2,4]triazolo[4,3-a][1,4]diazepin-4-yl)-N-ethylacetamide;
(S)-2-(6-(4-Chlorophenyl)-1-methyl-8-(3-(pyrrolidin-1-ylmethyl)phenyl)-4H-benzo[f][1,2,4]triazolo[4,3-a][1,4]diazepin-4-yl)-N-ethylacetamide;

(S)-2-(6-(4-Chlorophenyl)-1-methyl-8-(4-(pyrrolidin-1-ylmethyl)phenyl)-4H-benzo[f][1,2,4]triazolo[4,3-a][1,4]diazepin-4-yl)-N-ethylacetamide;

(S)-2-(6-(4-Chlorophenyl)-1-methyl-8-(4-((4-methylpiperazin-1-yl)methyl)phenyl)-4H-benzo[f][1,2,4]triazolo[4,3-a][1,4]diazepin-4-yl)-N-ethylacetamide;

(S)-2-(6-(4-Chlorophenyl)-8-(4-((ethylamino)methyl)phenyl)-1-methyl-4H-benzo[f][1,2,4]triazolo[4,3-a][1,4]diazepin-4-yl)-N-ethylacetamide;

(S)-2-(6-(4-Chlorophenyl)-8-(4-((dimethylamino)methyl)phenyl)-1-methyl-4H-benzo[f][1,2,4]triazolo[4,3-a][1,4]diazepin-4-yl)-N-ethylacetamide; and (S)-2-(6-(4-Chlorophenyl)-1-methyl-8-(2H-tetrazol-5-yl)-4H-benzo[f][1,2,4]triazolo[4,3-a][1,4]diazepin-4-yl)-N-ethylacetamide or a salt thereof.

29. A pharmaceutical composition which comprises a compound or a salt according to claim 1 wherein said salt is a pharmaceutically acceptable salt, and one or more pharmaceutically acceptable carriers, diluents or excipients.

* * * * *